United States Patent

Traxler et al.

[11] Patent Number: 5,981,533
[45] Date of Patent: Nov. 9, 1999

[54] PYRAZOLE DERIVATIVES AND PROCESSES FOR THE PREPARATION THEREOF

[75] Inventors: Peter Traxler, Schönenbuch, Switzerland; Pascal Furet, Thann, France; Guido Bold, Gipf-Oberfrick; Jörg Frei, Hölstein, both of Switzerland; Marc Lang, Mulhouse, France

[73] Assignee: Novartis AG, Basel, Switzerland

[21] Appl. No.: 08/930,904

[22] PCT Filed: Mar. 22, 1996

[86] PCT No.: PCT/EP96/01263

§ 371 Date: Oct. 3, 1997

§ 102(e) Date: Oct. 3, 1997

[87] PCT Pub. No.: WO96/31510

PCT Pub. Date: Oct. 10, 1996

[30] Foreign Application Priority Data

Apr. 3, 1995 [CH] Switzerland ............................... 937/95
Feb. 16, 1996 [CH] Switzerland ............................... 421/96

[51] Int. Cl.⁶ ........................ A61K 31/505; C07D 487/04
[52] U.S. Cl. ........................................... 514/258; 544/262
[58] Field of Search ............................... 544/262; 514/258

[56] References Cited

U.S. PATENT DOCUMENTS 5,686,457  11/1997  Traxler et al. .......................... 514/258

FOREIGN PATENT DOCUMENTS

| 566226 | 10/1993 | European Pat. Off. |
| 92/20642 | 11/1992 | WIPO |
| 95/19774 | 7/1995 | WIPO |
| 95/19970 | 7/1995 | WIPO |
| 9640142 | 12/1996 | WIPO |
| 98/14449 | 4/1998 | WIPO |
| 98/14450 | 4/1998 | WIPO |
| 98/14551 | 4/1998 | WIPO |

OTHER PUBLICATIONS

G. Dodin, et al., vol. 99, pp. 7257–7265, J. Am. Chem. Soc., 1977.
K. Klem, vol. 114, No. 6, pp. 2001–2018, Chem. Ber., 1981.
Traxler et al., "Use of Pharmacophore Model for the Design of EGF–R Tyrosine Kinase Inhibitors: 4–(Phenylamino) pyrazolo[3,4–d]pyrimidines," J. Med. Chem., vol. 40, No. 22, pp. 3601–3616, Oct. 24, 1997.
Burke, "Protein–Tyrosine Kinases: Potential Targets for Anticancer Drug Development," Stem Cells, vol. 12, pp. 1–6, 1994.

Primary Examiner—Mukund J. Shah
Assistant Examiner—Ann M. Kessinger
Attorney, Agent, or Firm—Joseph J. Borovian

[57] ABSTRACT

4-Amino-1H-pyrazolo[3,4-d]pyrimidine derivatives of formula I

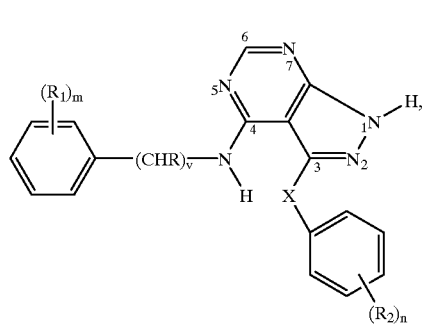

wherein the symbols are as defined in claim 1, and intermediates for their manufacture are described.

The compounds of formula I inhibit especially the tyrosine kinase activity of the receptor for epidermal growth factor and can be used, for example, in the case of epidermal hyperproliferation (psoriasis) and as anti-tumor agents.

12 Claims, No Drawings

PYRAZOLE DERIVATIVES AND PROCESSES FOR THE PREPARATION THEREOF

The invention relates to 4-amino-1H-pyrazolo[3,4-d] pyrimidine derivatives and intermediates and to processes for the preparation thereof, to pharmaceutical formulations comprising such derivatives, and to the use of those derivatives as medicaments.

The invention relates to 4-amino-1H-pyrazolo[3,4-d] pyrimidine derivatives of formula I

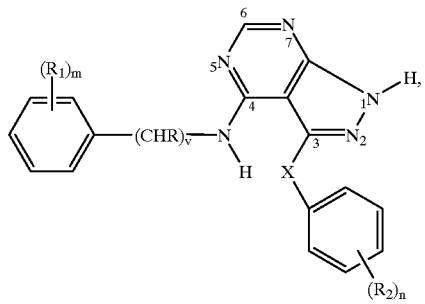

(I)

wherein
  m and n are each independently of the other an integer from 0 up to and including 3,
  v is 0 or 1,
  R is hydrogen or lower alkyl,
  $R_1$ is halogen, cyano, trifluoromethyl, hydroxy, lower alkoxy, lower alkanoyloxy, carboxy, lower alkoxycarbonyl, carbamoyl, N-lower alkylcarbamoyl, or lower alkyl that is unsubstituted or substituted by amino or by cyano, it being possible when several phenyl substituents $R_1$ are present for those substituents to be identical or different from one another,
  X is the group NH(CH—$R_7$)$_t$ wherein t is an integer from 0 up to and including 3 and $R_7$ is hydrogen or lower alkyl, or the group (C[$R_3$]—$R_4$)$_q$ wherein q is an integer from 0 up to and including 3, $R_3$ is hydrogen or lower alkyl and $R_4$ is hydrogen or lower alkyl, and $R_2$ is halogen, nitro, cyano, trifluoromethyl, carboxy, lower alkoxycarbonyl, carbamoyl, N-lower alkylcarbamoyl, N,N-di-lower alkylcarbamoyl, azido, amino, lower alkylamino, di-lower alkylamino, di-lower alkylamino-lower alkyleneamino, benzylamino; acylated or sulfonated amino each having up to 10 carbon atoms; hydroxy, lower alkanoyloxy, oxa-lower alkoxy, lower alkoxy that is unsubstituted or substituted by carboxy, lower alkoxycarbonyl, carbamoyl or by N-lower alkylcarbamoyl, or lower alkyl that is unsubstituted or substituted by amino, lower alkanoylamino, benzoylamino, lower alkoxycarbonylamino, sulfonated amino, cyano, hydroxy, lower alkanoyloxy, lower alkoxycarbonyloxy or by lower alkoxy, it being possible when several phenyl substituents $R_2$ are present for those substituents to be identical or different from one another and for two vicinal radicals $R_2$ together also to form methylenedioxy, and to salts and tautomers of such compounds.

When m or n is 0, the phenyl ring in question does not carry a substituent $R_1$ or $R_2$, respectively. Preferably, m and n are each independently of the other an integer from 0 up to and including 2. When m and/or n is/are 1, the phenyl substituent $R_1$ and/or $R_2$ is/are primarily in the 4-position, i.e. in the para-position, or especially in the 3-position, i.e. in the meta-position. When m and/or n is/are 2, the two phenyl substituents $R_1$ and/or $R_2$ are preferably in the 3- and 4-positions.

When v is 0, the (R$_1$)$_m$ phenyl radical is bonded directly to the nitrogen atom in the 4-position of the 1H-pyrazolo [3,4-d]pyrimidine derivative.

Halogen $R_1$ or $R_2$ is fluorine, bromine, iodine or, preferably, chlorine.

Lower alkoxy $R_1$ or $R_2$ is, for example, methoxy.

Lower alkanoyloxy $R_1$ or $R_2$ is, for example, acetoxy.

Lower alkoxycarbonyl $R_1$ or R2 is, for example, methoxycarbonyl.

N-Lower alkylcarbamoyl $R_1$ or $R_2$ is, for example, N-methylcarbamoyl.

Lower alkyl $R_1$ or $R_2$ that is substituted by amino or by cyano is, for example, —(CH$_2$)$_x$—NH$_2$ or —(CH$_2$)$_x$—CN, wherein x is in each case from 1 to 4.

The group NH(CH—$R_7$)$_t$ that is represented by the symbol X represents, when t is 0, the bivalent group NH. When t is from 1 to 3 and $R_7$ is hydrogen, the group NH(CH—$R_7$)$_t$ represents the bivalent radicals NHCH$_2$, NH—CH$_2$—CH$_2$ and NH—CH$_2$—CH$_2$—CH$_2$, respectively, each of which is bonded by its nitrogen atom to the pyrazole ring and by its terminal carbon atom to the phenyl ring. When t is 1 and $R_7$ is lower alkyl, the group NH(CH—$R_7$)$_t$ represents the bivalent radical NH—CH(lower alkyl), for example the radical NH—CH(CH$_3$). X is preferably NH, NH—CH$_2$ or NH—CH (CH$_3$).

The group (C[$R_3$]—$R_4$)$_q$ that is represented by the symbol X is, when q is 1, bonded by the underlined carbon atom ( C[$R_3$]—$R_4$)$_q$ both to the pyrazole ring and to the phenyl ring and is preferably CH$_2$ or CH(lower alkyl). When q in the group (C[$R_3$]—$R_4$)$_q$ is 2 or 3, the two free valencies originate from different carbon atoms, such as, for example, in dimethylene or trimethylene. When q is 0, the phenyl radical is bonded directly to the pyrazole ring.

Lower alkylamino $R_2$ is, for example, methylamino.

Di-lower alkylamino-lower alkyleneamino $R_2$ is a radical of the formula

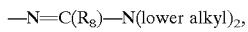

—N=C(R$_8$)—N(lower alkyl)$_2$, wherein $R_8$ is hydrogen or lower alkyl, and is especially di-lower alkylaminomethyleneamino, such as dimethylaminomethyleneamino of the formula (CH$_3$)$_2$N—CH=N—.

Acylated amino having up to 10 carbon atoms $R_2$ is, for example, unsubstituted or substituted lower alkanoylamino, benzoylamino, lower alkoxycarbonylamino, benzyloxycarbonylamino or monocyclic five- or six-membered heterocyclylcarbonylamino. Unsubstituted lower alkanoylamino is, for example, formylamino, acetylamino, propionylamino, 3-methylbutanoylamino or pivaloylamino. In such a substituted lower alkanoylamino radical the substituted lower alkanoyl radical is derived preferably from a naturally occurring amino acid, especially from one of the 20 amino acids that occur regularly in proteins, such as glycine, alanine, phenylalanine, etc. Preferred substituents in such a substituted lower alkanoylamino radical $R_2$ are therefore amino and, possibly, also hydroxy, mercapto, methylthio, carboxy, carbamoyl, phenyl, 4-hydroxy-phenyl, imidazolyl or indolyl. Lower alkoxycarbonylamino is, for example, tert-butyloxycarbonylamino. Monocyclic five- or six-membered heterocyclylcarbonylamino is, for example, thien-2-ylcarbonylamino, fur-2-ylcarbonylamino or pyrid-2-ylcarbonylamino.

Sulfonated amino having up to 10 carbon atoms $R_2$ is, for example, lower alkylsulfonylamino, such as especially methylsulfonylamino, or unsubstituted or substituted, for example lower alkyl-substituted, benzenesulfonylamino, such as p-toluenesulfonylamino.

Oxa-lower alkoxy is a lower alkoxy radical wherein one or more carbon atoms that are not adjacent to one another and that are other than C-1 have been replaced by oxygen, for example —O—CH$_2$—OCH$_3$, —O—CH$_2$—O—CH$_2$—CH$_3$, —O—CH$_2$—CH$_2$—OCH$_3$ or —O—CH$_2$—CH$_2$—O—CH$_2$—CH$_2$—OCH$_3$.

Lower alkoxy R$_2$ that is substituted by carboxy, lower alkoxycarbonyl, carbamoyl or by N-lower alkylcarbamoyl is, for example, carboxymethoxy, lower alkoxycarbonylmethoxy, carbamoylmethoxy, N-lower alkylcarbamoylmethoxy or ethoxy or n-propyloxy that is correspondingly substituted in the 2- or 3-position, respectively, i.e. in the ω-position.

Lower alkyl R$_2$ that is substituted by amino or by hydroxy is, for example, aminomethyl or hydroxymethyl.

Two vicinal radicals R$_2$ that together are methylenedioxy may be in the 2,3- or 3,4-position. 2,3-Methylenedioxyphenyl is benzo[1,3]dioxol-4-yl. 3,4-Methylenedioxyphenyl is benzo-[1,3]dioxol-5-yl.

Within the context of the present invention, the general terms used hereinbefore and hereinafter are preferably defined as follows:

The prefix "lower " denotes a radical having up to and including a maximum of 7, especially up to and including a maximum of 4, and above all 1 or 2, carbon atoms.

Halogen is preferably fluorine, chlorine, bromine or iodine, especially fluorine, chlorine or bromine, more especially bromine and above all chlorine.

Alkyl is unbranched or mono- or poly-branched and has preferably up to a maximum of 20 carbon atoms. Preference is given to lower alkyl, especially n-propyl, isopropyl, n-butyl, isobutyl, sec-butyl, tert-butyl, n-pentyl, neopentyl, n-hexyl, more especially ethyl and above all methyl.

Alkoxy contains an alkyl radical as last defined and is especially lower alkoxy, such as n-propoxy, isopropoxy, n-butoxy, isobutoxy, sec-butoxy, tert-butoxy, n-pentyloxy, neopentyloxy, n-hexyloxy, especially ethoxy and above all methoxy.

Since compounds of formula I have basic properties, salts of those compounds are acid addition salts with organic or inorganic acids, especially the pharmaceutically acceptable, non-toxic salts. Suitable inorganic acids are, for example, carbonic acid (preferably in the form of the carbonates or hydrogen carbonates); hydrohalic acids, such as hydrochloric acid; sulfuric acid; or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, 2-hydroxybutyric acid, gluconic acid, glucosemonocarboxylic acid, fumaric acid, succinic acid, adipic acid, pimelic acid, suberic acid, azelaic acid, malic acid, tartaric acid, citric acid, glucaric acid, galactaric acid, amino acids, such as glutamic acid, aspartic acid, N-methylglycine, acetylaminoacetic acid, N-acetylasparagine or N-acetylcystine, pyruvic acid, acetoacetic acid, phosphoserine, 2- or 3-glycerophosphoric acid, glucose-6-phosphoric acid, glucose-1-phosphoric acid, fructose-1,6-bis-phosphoric acid, maleic acid, hydroxymaleic acid, methylmaleic acid, cyclohexanecarboxylic acid, adamantanecarboxylic acid, benzoic acid, salicylic acid, 1- or 3-hydroxynaphthyl-2-carboxylic acid, 3,4,5-trimethoxybenzoic acid, 2-phenoxybenzoic acid, 2-acetoxybenzoic acid, 4-aminosalicylic acid, phthalic acid, phenylacetic acid, mandelic acid, cinnamic acid, nicotinic acid, isonicotinic acid, glucuronic acid, galacturonic acid, methane or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. Only salts that are pharmaceutically acceptable and non-toxic (at the appropriate dosages) are used therapeutically and those salts are therefore preferred.

It is possible that the compounds of the formula I and the intermediates containing the pyrazole moiety are present under certain conditions, e.g. when dissolved in certain solvents, to some extent in a tautomeric form wherein the nitrogen normally located at the nitrogen atom in position 1 of the pyrazole moiety is translocated to another suitable nitrogen atom, e.g. the nitrogen atoms in positions 2, 5 or 7 of formula I. The invention relates also to these tautomers.

The compounds of formula I have valuable pharmacologically useful properties. In particular they exhibit specific inhibitory activities that are of pharmacological interest. They are effective especially as protein tyrosine kinase inhibitors and/or (furthermore) as inhibitors of protein serine/threonine kinases; they exhibit, for example, powerful inhibition of the tyrosine kinase activity of the receptor for epidermal growth factor (EGF) and of c-erbB2-kinase. Those receptor-specific enzyme activities play a key role in signal transmission in a large number of mammalian cells, including human cells, especially epithelial cells, cells of the immune system and cells of the central and peripheral nervous system. For example, in various cell types, EGF-induced activation of receptor-associated protein tyrosine kinase (EGF-R-PTK) is a prerequisite for cell division and hence for the proliferation of the cell population. The administration of EGF-receptor-specific tyrosine kinase inhibitors thus inhibits the proliferation of the cells. The same applies analogously to the other protein kinases mentioned hereinbefore and hereinafter.

The inhibition of EGF-receptor-specific protein tyrosine kinase (EGF-R-PTK) can be demonstrated using known methods, for example using the recombinant intracellular domain of the EGF-receptor (EGF-R ICD; see, for example, E. McGlynn et al., Europ. J. Biochem. 207, 265–275 (1992)). Compared with the control without inhibitor, the compounds of formula I inhibit the enzyme activity by 50% (IC$_{50}$), for example in a concentration of from 0.0005 to 5 μM, especially from 0.001 to 0.1 μM.

In addition to or instead of inhibiting EGF-receptor tyrosine protein kinase, the compounds of formula I also inhibit to a varying extent other tyrosine protein kinases that are involved in signal transmission mediated by trophic factors, for example abl kinase, especially v-abl kinase, kinases from the family of the src kinases, especially c-src kinase, lck, fyn; further kinases of the EGF family, for example c-erbB2 kinase (HER-2), c-erbB3 kinase, c-erbB4 kinase; members of the PDGF receptor tyrosine protein kinase family, for example the PDGF receptor kinase, the (CSF-1 receptor kinase, the Kit receptor kinase, the VEGF receptor kinase and the FGF receptor kinase; the insulin-like growth factor receptor kinase (IGF-1 kinase), as well as serine/threonine kinases, for example protein kinase C or CDC kinases, all of which play a part in growth regulation and transformation in mammalian cells, including human cells.

The inhibition of c-erbB2-tyrosine kinase (HER-2) can be determined, for example, analogously to the method used for EGF-R-PTK (see C. House et al., Europ. J. Biochem. 140, 363–367 (1984)). The c-erbB2-kinase can be isolated, and its activity determined, by means of protocols known per se, for example in accordance with T. Akiyama et al., Science 232, 1644 (1986).

In the micromolar range too, the compounds of formula I exhibit, for example, inhibition of the cell growth of EGF-dependent cell lines, for example the epidermoid BALB/c mouse keratinocyte cell line (see Weissmann, B. A., and Aaronson, S. A., Cell 32, 599 (1983)) or the A431 cell line, which are recognized useful standard sources of EGF-dependent epithelial cells (see Carpenter, G., and Zendegni, J. Anal. Biochem. 153, 279–282 (1985)). In a known test method (see Meyer et al., Int. J. Cancer 43, 851 (1989)), the inhibitory activity of the compounds of formula I is determined, briefly, as follows: BALB/MK cells (10 000/microtiter plate well) are transferred to 96-well microtiter plates. The test compounds (dissolved in DMSO) are added in a series of concentrations (dilution series) in such a manner that the final concentration of DMSO is not greater than 1% (v/v). After the addition, the plates are incubated for three days during which the control cultures without test compound are able to undergo at least three cell-division cycles. The growth of the MK cells is measured by means of methylene blue staining: after the incubation the cells are fixed with glutaraldehyde, washed with water and stained with 0.05% methylene blue. After a washing step the stain is eluted with 3% HCl and the optical density per well of the microtiter plate is measured using a Titertek multiskan at 665 nm. $IC_{50}$ values are determined by a computer-aided system using the formula:

$$IC_{50}=[(OD_{test}-OD_{start})/(OD_{control}-OD_{start})]\times 100.$$

The $IC_{50}$ value in those experiments is given as that concentration of the test compound in question that results in a cell count that is 50% lower than that obtained using the control without inhibitor. The compounds of formula I exhibit inhibitory activity in the micromolar range, for example an $IC_{50}$ of approximately from 0.1 to 10 μM, especially from 0.4 to 4 μM.

The compounds of formula I exhibit inhibition of the growth of tumor cells also in vivo, as shown, for example, by the test described below: the test is based on inhibition of the growth of the human epidermoid carcinoma A431 (ATCC No. CRL 1555; American Type Culture Collection, Rockville, Md., USA; see Santon, J. B., et al., Cancer Research 46, 4701–4705 (1986) and Ozawa, S., et al., Int. J. Cancer 40, 706–710 (1987)), which is transplanted into female BALB/c nude mice (Bomholtgard, Denmark). That carcinoma exhibits a growth that correlates with the extent of the expression of EGF-receptor. In the experiment, tumors having a volume of approximately 1 cm³ cultured in vivo are surgically removed from experimental animals under sterile conditions. The tumors are comminuted and suspended in 10 volumes (w/v) of phosphate-buffered saline. The suspension is injected s.c. (0.2 ml/mouse in phosphate-buffered saline) into the left flank of the animals. Alternatively, $1\times 10^6$ cells from an in vitro culture can be injected in 0.2 ml of phosphate-buffered saline. Treatment with test compounds of formula I is started 5 or 7 days after the transplant, when the tumors have reached a diameter of 4–5 mm. The test compound in question is administered (in different doses for different animal groups) once a day for 15 successive days. The tumor growth is determined by measuring the diameter of the tumors along three axes that are perpendicular to each other. The tumor volumes are calculated using the known formula $p\times L\times D^2/6$ (see Evans, B. D., et al., Brit. J. Cancer 45, 466–8 (1982)). The results are given as treatment/control percentages (T/C×100=T/C %). At a dose of from 3 to 50 mg/kg of active ingredient, distinct inhibition of the tumor growth is found, for example T/C % values of less than 10, which indicates strong inhibition of tumor growth.

The compounds of formula I which inhibit the tyrosine kinase activity of the receptor for the epidermal growth factor (EGF) or also of the other protein kinases mentioned are therefore useful, for example, in the treatment of benign or malignant tumors. They are capable of effecting tumor regression and of preventing the formation of tumor metastases, the growth of micrometastases and the formation of new blood vessels (angiogenesis) required for tumor growth. They can be used especially in the case of epidermal hyperproliferation (psoriasis), in the treatment of neoplasia of epithelial character, e.g. mammary or ovarian carcinomas, and in leukemias. In addition, the compounds of formula I (especially the novel compounds) can be used in the treatment of disorders of the immune system in which several or, preferably, individual protein tyrosine kinases and/or (furthermore) protein serine/threonine kinases are involved; those compounds of formula I can also be used in the treatment of disorders of the central or peripheral nervous system in which signal transmission by several or, preferably, a single protein tyrosine kinase(s) and/or (furthermore) protein serine/threonine kinase(s) is/are involved.

In general, the present invention relates also to the use of the compounds of formula I in the inhibition of the mentioned protein kinases.

The compounds according to the invention can be used both alone and in combination with other pharmacologically active compounds, for example together with inhibitors of the enzymes of polyamine synthesis, inhibitors of protein kinase C, inhibitors of other tyrosine kinases, cytokines, negative growth regulators, for example TGF-β or IFN-β, aromatase inhibitors, antiestrogens and/or cytostatic agents.

In the case of the preferred subjects of the invention mentioned hereinafter, general definitions can be replaced by the more specific definitions given at the beginning, where appropriate and expedient.

Preference is given to compounds of formula I according to claim 1, wherein $R_2$ is halogen, nitro, cyano, trifluoromethyl, carboxy, lower alkoxycarbonyl, carbamoyl, N-lower alkylcarbamoyl, N,N-di-lower alkylcarbamoyl, azido, amino, lower alkylamino, di-lower alkylamino, di-lower alkylamino-lower alkyleneamino, benzylamino, benzoylamino, lower alkanoylamino, lower alkoxycarbonylamino, benzyloxycarbonylamino, thien-2-ylcarbonylamino, fur-2-ylcarbonylamino, pyrid-2-ylcarbonylamino, lower alkylsulfonylamino, benzenesulfonylamino, p-toluenesulfonylamino, hydroxy, lower alkanoyloxy, oxa-lower alkoxy, lower alkoxy that is unsubstituted or substituted by carboxy, lower alkoxycarbonyl, carbamoyl or by N-lower alkylcarbamoyl, or lower alkyl that is unsubstituted or substituted by amino, lower alkanoylamino, benzoylamino, lower alkoxycarbonylamino, lower alkylsulfonylamino, benzenesulfonylamino, p-toluenesulfonylamino, cyano, hydroxy, lower alkanoyloxy, lower alkoxycarbonyloxy or by lower alkoxy, it being possible when several phenyl substituents $R_2$ are present for those substituents to be identical or different from one another and for two vicinal radicals $R_2$ together also to form methylenedioxy, and the remaining symbols are as defined above, and to salts of such compounds.

Preference is given to compounds of formula I according to claim 1, wherein
  m is 0 or 1,
  n is an integer from 0 up to and including 3,
  v is 0 or 1,
  R is hydrogen or lower alkyl,
  $R_1$ is halogen or lower alkyl that is unsubstituted or substituted by amino or by cyano,
  X is the group NH(CH—$R_7$)$_t$ wherein t is 0 or 1 and $R_7$ is hydrogen or lower alkyl, or the group (C[$R_3$]—$R_4$)$_q$ wherein q is 0, and
  $R_2$ is halogen, nitro, carboxy, lower alkoxycarbonyl, carbamoyl, N-lower alkylcarbamoyl, N,N-di-lower alkylcarbamoyl, amino, lower alkylamino, di-lower alkylamino, di-lower alkylaminomethyleneamino, benzylamino, benzoylamino, lower alkanoylamino, lower alkoxycarbonylamino, benzyloxycarbonylamino, thien-2-yl-carbonylamino, fur-2-ylcarbonylamino, pyrid-2-ylcarbonylamino, lower alkylsulfonylamino, benzenesulfonylamino, p-toluenesulfonylamino, hydroxy, lower alkanoyloxy, lower alkoxy, or lower alkyl that is unsubstituted or substituted by amino, lower alkanoylamino, benzoylamino or by lower alkoxycarbonylamino, it being possible when several phenyl substituents $R_2$ are present for those substituents to be identical or different from one another and for two vicinal radicals $R_2$ together also to form methylenedioxy,
and to salts of such compounds.

Preference is given also to 4-phenylamino-1H-pyrazolo [3,4-d]pyrimidine derivatives of formula Ia

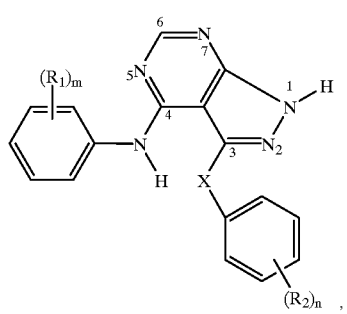

(Ia)

wherein
  m and n are each independently of the other an integer from 0 up to and including 3,
  $R_1$ is halogen, cyano, trifluoromethyl, hydroxy, lower alkoxy, lower alkanoyloxy, carboxy, lower alkoxycarbonyl, carbamoyl, N-lower alkylcarbamoyl, or lower alkyl that is unsubstituted or substituted by amino or by cyano, it being possible when several phenyl substituents $R_1$ are present for those substituents to be identical or different from one another,
  X is the group NH(CH$_2$)$_t$ wherein t is an integer from 0 up to and including 3, or the group (C[$R_3$]—$R_4$)$_q$ wherein q is an integer from 0 up to and including 3, $R_3$ is hydrogen or lower alkyl and $R_4$ is hydrogen or lower alkyl, and
  $R_2$ is halogen, nitro, cyano, trifluoromethyl, carboxy, lower alkoxycarbonyl, carbamoyl, N-lower alkylcarbamoyl, amino, lower alkylamino, acylated amino having up to 10 carbon atoms, hydroxy, lower alkanoyloxy, oxa-lower alkoxy, lower alkoxy that is unsubstituted or substituted by carboxy, lower alkoxycarbonyl, carbamoyl or by N-lower alkylcarbamoyl, or lower alkyl that is unsubstituted or substituted by amino or by hydroxy, it being possible when several phenyl substituents $R_2$ are present for those substituents to be identical or different from one another, and to salts of such compounds.

Preference is given to compounds of formula Ia wherein X is the group NH(CH$_2$)$_t$ wherein t is an integer from 0 up to and including 3, or the group (C[$R_3$]—$R_4$)$_q$ wherein q is 0, and the remaining symbols are as defined above, and to salts of those compounds.

Preference is given especially to compounds of formula Ia wherein X is the group NH(CH$_2$)$_t$ wherein t is 0, and the remaining symbols are as defined above, and to salts of those compounds.

Special preference is given to compounds of formula Ia wherein m and n are each independently of the other 0 or 1, $R_1$ is halogen, or lower alkyl that is unsubstituted or substituted by amino or by cyano, X is the group NH(CH$_2$)$_t$ wherein t is 0, and $R_2$ is halogen or lower alkoxy, and to salts of those compounds.

Special preference is given also to compounds of formula Ia wherein m is 1 and $R_1$ is 3-chloro, and to salts of those compounds.

Preference is given above all to the compounds of formula I mentioned in the Examples and to the pharmaceutically acceptable salts thereof.

The compounds of formula I and the salts thereof can be prepared in a manner known per se. The preparation process according to the invention comprises a) treating a compound of formula II

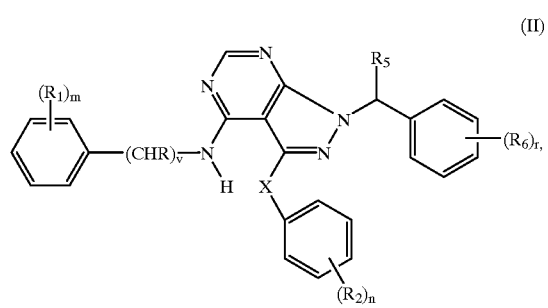

(II)

wherein $R_5$ is hydrogen or methyl, $R_6$ is alkoxy having from 1 to 3 carbon atoms or is nitro, r is an integer from 0 to 2, and the remaining substituents and symbols are as defined above, with a suitable Lewis acid, or b) reacting a compound of formula XV

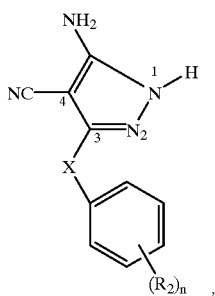
(XV)

wherein the symbols are as defined above, with an amine of formula XVI

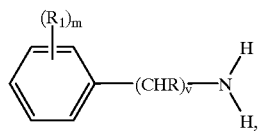
(XVI)

wherein v is 1 and the remaining symbols are as defined above, or with a salt thereof, in the presence of formic acid, or c) reacting a compound of formula XV

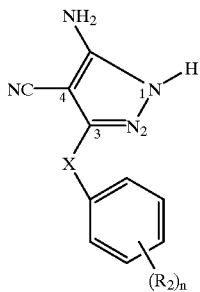
(XV)

wherein the symbols are as defined above, with a formamide derivative of formula XVII

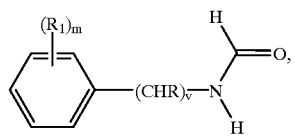
(XVII)

wherein v is 1 and the remaining symbols are as defined above, or d) reacting a compound of formula XVIII

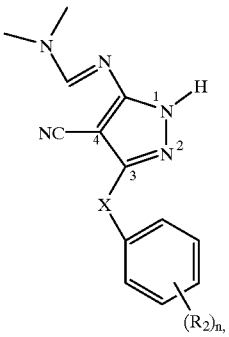
(XVIII)

wherein the symbols are as defined above, with an amine of formula XVI

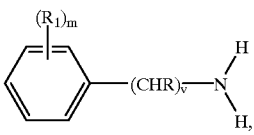
(XVI)

wherein v is 0 or 1 and the remaining symbols are as defined above, or with a salt thereof, or e) subjecting a compound of formula XIX

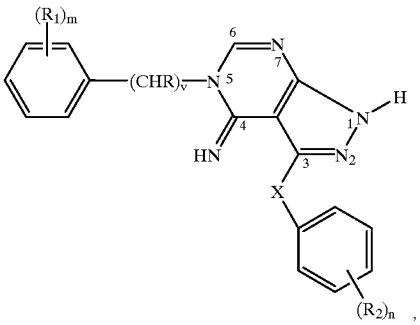
(XIX)

wherein the symbols are as defined above, to the conditions of a Dimroth rearrangement, and, if desired, converting a compound of formula I obtainable in accordance with any one of processes a) to e) into its salt, or converting an obtainable salt of a compound of formula I into the free compound.

The procedure for those process variants and the preparation of the starting materials are described in more detail below:

GENERAL POINTS

If necessary, interfering functional groups in starting materials are protected before the reaction, in a manner known per se, by readily removable protecting groups which are removed again when the reaction has taken place.

Process a):

When $R_5$ is hydrogen, a suitable Lewis acid is especially aluminum chloride. The reaction is carried out in an inert organic solvent, for example a hydrocarbon, such as, preferably, an aromatic hydrocarbon, such as especially benzene or toluene, at a temperature of from room temperature (approx. 20° C.) to +200° C., if necessary under a protective gas, such as argon, and/or under increased pressure, preferably at the boiling temperature of the solvent used, that is to say under reflux. When $R_5$ is methyl, boiling is preferably carried out with polyphosphoric acid.

The starting material of formula II is obtained as follows: first a compound of formula III

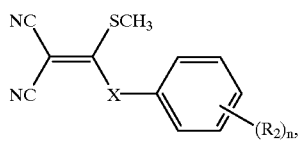

(III)

wherein X, $R_2$ and n are as defined above, is reacted with a hydrazine derivative of formula IV

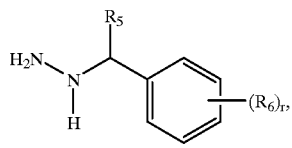

(IV)

wherein $R_5$ is hydrogen or methyl, $R_6$ is alkoxy having from 1 to 3 carbon atoms or is nitro, and r is an integer from 0 to 2, or (in the presence of a suitable base, like sodium methylate) with a salt thereof, to form a pyrazole derivative of formula V

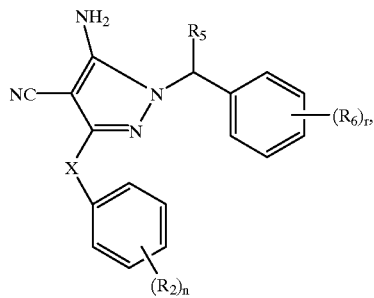

(V)

wherein the substituents are as defined above. For example, there is used as starting material a solution in methanol of a hydrazine derivative of formula IV in the form of the dihydrochloride, to which there is added first, with cooling, for example with ice, a solution of sodium methanolate in methanol and then, at room temperature, a solution of a compound of formula III in a suitable anhydrous alcohol, such as absolute ethanol. Heating is then carried out for several hours under reflux.

The resulting compound of formula V is reacted with formic acid with synthesis of the pyrimidine ring to form a compound of formula VI

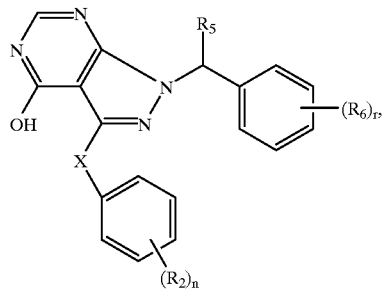

(VI)

wherein the substituents are as defined above. Preferably, a compound of formula V is heated under reflux for several hours in 85% aqueous formic acid.

From a compound of formula VI there is obtained with phosphoryl chloride (phosphorus oxychloride, $POCl_3$) or phosphorus trichloride ($PCl_3$), with replacement of the hydroxy group by chlorine, a compound of formula VII

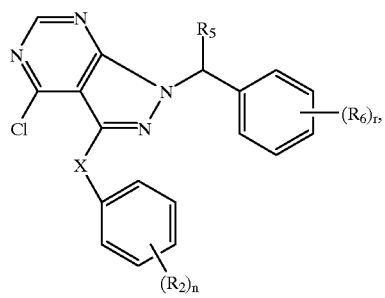

(VII)

wherein the substituents are as defined above. Preferably, a compound of formula VI is heated under reflux for several hours in phosphoryl chloride under a protective gas, such as argon.

A compound of formula VII is then reacted with an aniline derivative of formula VIII

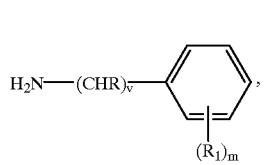

(VIII)

wherein the symbols are as defined above, preferably in a suitable solvent, such as a suitable alcohol, e.g. ethanol, under a protective gas, such as nitrogen, at elevated temperature, for example under reflux, to form the desired starting material of formula II.

The starting material of formula III wherein X is the group $NH(CH_2)_t$ wherein t is as defined above is obtained, for example, by reacting 3,3-bis-methylmercapto-2-cyano-acrylonitrile of formula IX

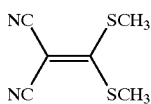
(IX)

with an amine of formula X

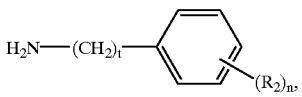
(X)

wherein the symbols are as defined above. The above-mentioned 3,3-bis-methyl-mercapto-2-cyano-acrylonitrile of formula IX is described under the name 2,2-bis-methylmercapto-1-cyano-acrylonitrile' by R. Gompper and W. Töpel, Chem. Ber. 95, 2861–2870, especially in the middle of page 2868, and can be prepared at a temperature of from 5 to 20° C. by the addition of malonic acid dinitrile having the formula $CH_2(CN)_2$ to carbon disulfide in the presence of sodium methanolate in methanol, followed by methylation of the resulting intermediate with dimethyl sulfate.

The starting material of formula III wherein X is the group $(C[R_3]—R_4)_q$ wherein q is 0, and the remaining symbols are as defined above, that is to say a compound of formula IIIa

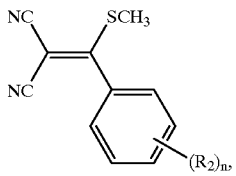
(IIIa)

wherein $R_2$ and n are as defined above, is obtained, for example, by reacting a compound of formula XI

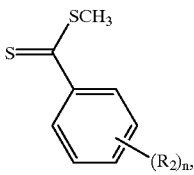
(XI)

wherein $R_2$ and n are as defined above, with the tetracyano epoxide of formula XII

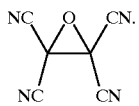
(XII)

The compounds of formula XI are obtained, for example, from an aldehyde of formula XIII

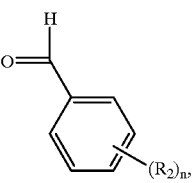
(XIII)

wherein $R_2$ and n are as defined above, which is first converted using sulfur and morpholine into a compound of formula XIV

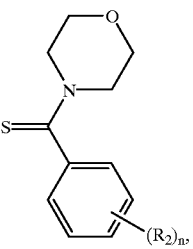
(XIV)

wherein $R_2$ and n are as defined above, which compound is then converted using methyl iodide in acetone, followed by hydrogen sulfide in pyridine, into a compound of formula XI.

Process b):

The starting material of formula XVI can be used in the form of a salt, for example in the form of an acetate. The reaction is carried out in formic acid at elevated temperature, preferably at 100–250° C., such as especially at 200° C.

The starting material of formula XV is obtained from a compound of formula III by reaction with hydrazine in a suitable solvent, such as a suitable alkanol, such as preferably methanol, for example at the reflux temperature.

Process c):

The reaction is carried out at elevated temperature, preferably at 100–250° C., such as especially at 200° C., in the presence or, where possible, in the absence of a solvent, i.e. the formamide derivative of formula XVII can be used simultaneously as the solvent.

Process d):

The reaction is carried out at elevated temperature, preferably at 50–180° C., such as especially at 120° C., in the presence or, where possible, in the absence of a solvent, i.e. the amine derivative of formula XVI can be used simultaneously as the solvent. When v is 0, the amine derivative of formula XVI is preferably used in the form of a salt, for example in the form of a hydrochloride. When v is 1, the amine derivative of formula XVI is preferably used in the form of the free amine.

The starting material of formula XVIII is obtained from a compound of formula XV by reaction with a suitable dimethylformamide acetal, such as N,N-dimethylformamide diethyl acetal, in a suitable solvent, such as a suitable aromatic hydrocarbon, such as especially toluene, at elevated temperature, preferably at 50–180° C., such as especially under reflux.

Process e):

The Dimroth rearrangement is carried out at elevated temperature, for example at 70–200° C., preferably at 80–150° C., for example under reflux, in a suitable water-containing solvent mixture, for example a mixture of water and a suitable ether, such as a cyclic ether, such as dioxane, for example a dioxane/water mixture in a ratio by volume of 1:1.

The imine of formula XIX is obtained, for example, from a compound of formula XV in two stages, as follows:

In the first stage, a compound of formula XV is reacted with orthoformic acid triethyl ester of formula $HC(OC_2H_5)_3$ to form an ethoxymethyleneamino compound of formula XX

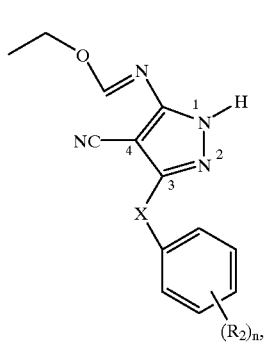

(XX)

wherein the symbols are as defined above.

The reaction is carried out at elevated temperature, preferably at 50–180° C., such as especially at 120° C., the orthoformic acid triethyl ester serving simultaneously as the solvent. The ethanol formed by the reaction is continuously distilled off from the reaction mixture.

In the second stage, the resulting compound of formula XX is reacted with an amine of formula XVI wherein v is 0 or 1 and the remaining symbols are as defined above to form the desired imine of formula XIX. The reaction is carried out in a suitable solvent, such as a suitable alcohol, for example an alkanol, such as preferably ethanol, at elevated temperature, preferably at 50–180° C., such as especially at 70–120° C., for example at the reflux temperature.

Alternatively, the imine of formula XIX is obtained directly from a compound of formula XVIII by reaction with an amine of formula XVI [similarly to process d)] in admixture with the end product of formula I. That reaction is carried out in a suitable solvent, such as a suitable alcohol, for example an alkanol, such as preferably ethanol, at elevated temperature, preferably at 50–180° C., such as especially at 70–120° C., for example at the reflux temperature.

Acid addition salts of compounds of formula I are obtained in a manner known per se, for example by treatment with an acid or a suitable anion exchange reagent.

Acid addition salts can be converted into the free compounds in customary manner, for example by treatment with a suitable basic agent.

Mixtures of isomers can be separated into the individual isomers in a manner known per se, for example by fractional crystallization, chromatography, etc.

The invention relates especially to a process for the preparation of a 4-phenylamino-1H-pyrazolo[3,4-d]pyrimidine derivative of formula Ia

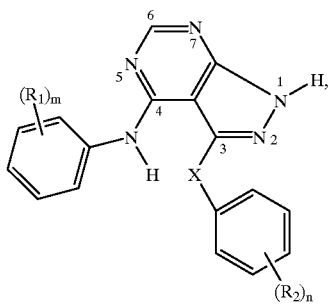

wherein
m and n are each independently of the other an integer from 0 up to and including 3,
$R_1$ is halogen, cyano, trifluoromethyl, hydroxy, lower alkoxy, lower alkanoyloxy, carboxy, lower alkoxycarbonyl, carbamoyl, N-lower alkylcarbamoyl, or lower alkyl that is unsubstituted or substituted by amino or by cyano, it being possible when several phenyl substituents $R_1$ are present for those substituents to be identical or different from one another,
X is the group $NH(CH_2)_t$ wherein t is an integer from 0 up to and including 3, or the group $(C[R_3]-R_4)_q$ wherein q is an integer from 0 up to and including 3, $R_3$ is hydrogen or lower alkyl and $R_4$ is hydrogen or lower alkyl, and
$R_2$ is halogen, nitro, cyano, trifluoromethyl, carboxy, lower alkoxycarbonyl, carbamoyl, N-lower alkylcarbamoyl, amino, lower alkylamino, acylated amino having up to 10 carbon atoms, hydroxy, lower alkanoyloxy, oxa-lower alkoxy, lower alkoxy that is unsubstituted or substituted by carboxy, lower alkoxycarbonyl, carbamoyl or by N-lower alkylcarbamoyl, or lower alkyl that is unsubstituted or substituted by amino or by hydroxy, it being possible when several phenyl substituents $R_2$ are present for those substituents to be identical or different from one another,
or a salt thereof,
which process comprises treating a compound of formula IIa

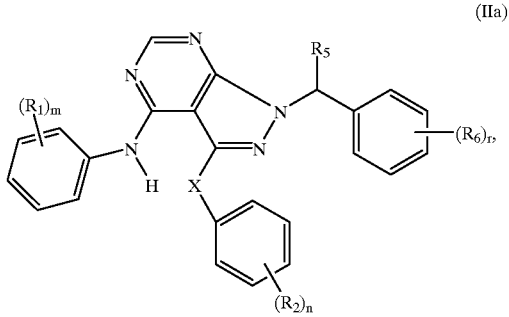

wherein $R_5$ is hydrogen or methyl,
$R_6$ is alkoxy having from 1 to 3 carbon atoms or is nitro,
r is an integer from 0 to 2,
and the remaining substituents and symbols are as defined above, with a suitable Lewis acid and, if desired, converting an obtainable compound of formula I into its salt, or converting an obtainable salt of a compound of formula I into the free compound.

The processes described above, including the processes for the removal of protecting groups and the additional process steps, are, unless otherwise indicated, carried out in a manner known per se, for example in the presence or absence of preferably inert solvents and diluents, if necessary in the presence of condensation agents or catalysts, at reduced or elevated temperature, for example in a temperature range of from approximately −20° C. to approximately 200° C. (preferably to 150° C.), especially from approximately 0° C. to approximately 120° C. (preferably to +70° C. or to +80° C.), preferably from approximately +10° C. to approximately +50° C., above all at room temperature, in a suitable vessel and, if necessary, under an inert gas atmosphere, for example a nitrogen atmosphere.

In those processes, taking into account all the substituents present in the molecule, if necessary, for example when readily hydrolyzable radicals are present, especially mild reaction conditions should be used, such as short reaction times, the use of mild acidic or basic agents at low concentrations, stoichiometric quantity ratios and the choice of suitable catalysts, solvents, temperature and/or pressure conditions.

The invention relates also to those forms of the process according to which a compound obtainable as intermediate at any stage of the process is used as starting material and the remaining process steps are carried out or the process is interrupted at any stage or a starting material is formed under the reaction conditions or is used in the form of a reactive derivative or salt. There are preferably used those starting materials which in accordance with the process result in the compounds described above as being especially valuable.

The present invention relates also to novel starting materials and/or intermediates and to processes for the preparation thereof. The starting materials used and the reaction conditions chosen are preferably those that result in the compounds described in this Application as being especially preferred.

The intermediates of formulae V, VI, VII, XVIII, XIX and XX wherein corresponding substituents have the meanings mentioned in this text for the compounds of the formula I are novel and the present invention relates also thereto. Preference is given to those intermediates that result in the preferred end products of formula I.

The invention relates to 5-amino-4-cyano-pyrazole derivatives of formula V

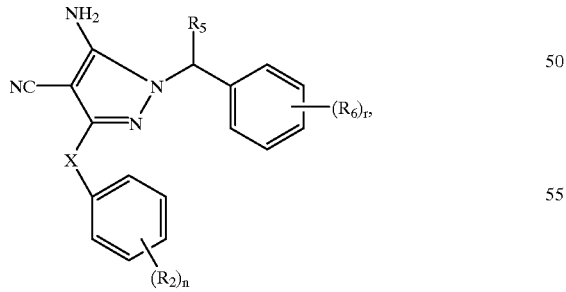

(V)

wherein n is an integer from 0 up to and including 3, r is an integer from 0 to 2, X is the group $NH(CH_2)_t$ wherein t is an integer from 0 up to and including 3, or the group $(C[R_3]-R_4)_q$ wherein q is an integer from 0 up to and including 3, $R_3$ is hydrogen or lower alkyl and $R_4$ is hydrogen or lower alkyl, $R_2$ is halogen, nitro, cyano, tri-fluoromethyl, carboxy, lower alkoxycarbonyl, carbamoyl, N-lower alkylcarbamoyl, amino, lower alkylamino, acylated amino having up to 10 carbon atoms, hydroxy, lower alkanoyloxy, oxa-lower alkoxy, lower alkoxy that is unsubstituted or substituted by carboxy, lower alkoxycarbonyl, carbamoyl or by N-lower alkylcarbamoyl, or lower alkyl that is unsubstituted or substituted by amino or by hydroxy, it being possible when several phenyl substituents $R_2$ are present for those substituents to be identical or different from one another, $R_5$ is hydrogen or methyl, and $R_6$ is alkoxy having from 1 to 3 carbon atoms or is nitro.

The invention relates also to compounds of formula XIX

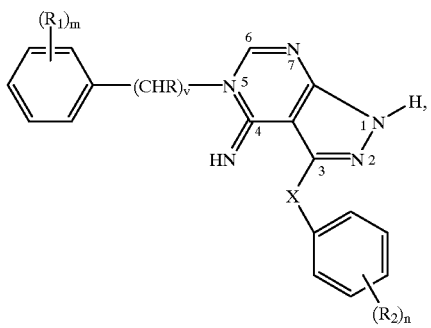

(XIX)

wherein m and n are each independently of the other an integer from 0 up to and including 3, v is 0 or 1, R is hydrogen or lower alkyl, $R_1$ is halogen, cyano, trifluoromethyl, hydroxy, lower alkoxy, lower alkanoyloxy, carboxy, lower alkoxycarbonyl, carbamoyl, N-lower alkylcarbamoyl, or lower alkyl that is unsubstituted or substituted by amino or by cyano, it being possible when several phenyl substituents $R_1$ are present for those substituents to be identical or different from one another, X is the group $NH(CH-R_7)_t$, wherein t is an integer from 0 up to and including 3 and $R_7$ is hydrogen or lower alkyl, or the group $(C[R_3]-R_4)_q$ wherein q is an integer from 0 up to and including 3, $R_3$ is hydrogen or lower alkyl and $R_4$ is hydrogen or lower alkyl, and $R_2$ is halogen, nitro, cyano, trifluoromethyl, carboxy, lower alkoxycarbonyl, carbamoyl, N-lower alkylcarbamoyl, N,N-di-lower alkylcarbamoyl, azido, amino, lower alkylamino, di-lower alkylamino, di-lower alkylamino-lower alkyleneamino, benzylamino; acylated or sulfonated amino each having up to 10 carbon atoms; hydroxy, lower alkanoyloxy, oxa-lower alkoxy, lower alkoxy that is unsubstituted or substituted by carboxy, lower alkoxycarbonyl, carbamoyl or by N-lower alkylcarbamoyl, or lower alkyl that is unsubstituted or substituted by amino, lower alkanoylamino, benzoylamino, lower alkoxycarbonylamino, sulfonated amino, cyano, hydroxy, lower alkanoyloxy, lower alkoxycarbonyloxy or by lower alkoxy, it being possible when several phenyl substituents $R_2$ are present for those substituents to be identical or different from one another and for two vicinal radicals $R_2$ together also to form methylenedioxy, and to salts of such compounds having salt-forming groups.

The compounds of the formula XIX can not only be used as intermediates but they exhibit also pharmacological activities similar to those of the end products of the formula I.

The invention relates also to 4-hydroxy-pyrazolo[3,4-d] pyrimidine derivatives of formula VI

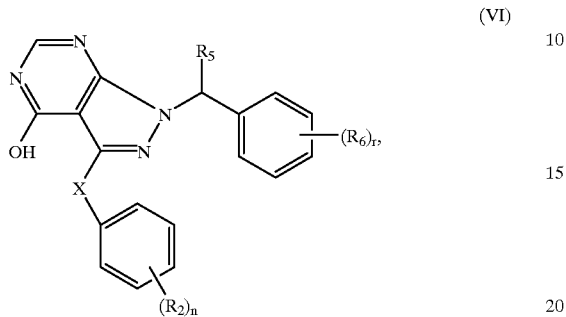

(VI)

wherein n is an integer from 0 up to and including 3,
r is an integer from 0 to 2,
X is the group $NH(CH_2)_t$ wherein t is an integer from 0 up to and including 3, or the group $(C[R_3]-R_4)_q$ wherein q is an integer from 0 up to and including 3, $R_3$ is hydrogen or lower alkyl and $R_4$ is hydrogen or lower alkyl,
$R_2$ is halogen, nitro, cyano, trifluoromethyl, carboxy, lower alkoxycarbonyl, carbamoyl, N-lower alkylcarbamoyl, amino, lower alkylamino, acylated amino having up to 10 carbon atoms, hydroxy, lower alkanoyloxy, oxa-lower alkoxy, lower alkoxy that is unsubstituted or substituted by carboxy, lower alkoxycarbonyl, carbamoyl or by N-lower alkylcarbamoyl, or lower alkyl that is unsubstituted or substituted by amino or by hydroxy, it being possible when several phenyl substituents $R_2$ are present for those substituents to be identical or different from one another,
$R_5$ is hydrogen or methyl, and
$R_6$ is alkoxy having from 1 to 3 carbon atoms or is nitro.

The invention relates also to 4-chloro-pyrazolo[3,4-d] pyrimidine derivatives of formula VII

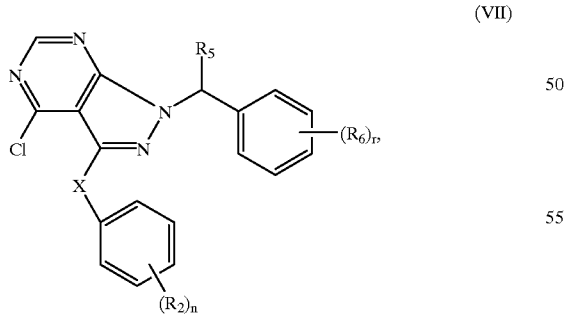

(VII)

wherein n is an integer from 0 up to and including 3,
r is an integer from 0 to 2,
X is the group $NH(CH_2)_t$ wherein t is an integer from 0 up to and including 3, or the group $(C[R_3]-R_4)_q$ wherein q is an integer from 0 up to and including 3, $R_3$ is hydrogen or lower alkyl and $R_4$ is hydrogen or lower alkyl,
$R_2$ is halogen, nitro, cyano, trifluoromethyl, carboxy, lower alkoxycarbonyl, carbamoyl, N-lower alkylcarbamoyl, amino, lower alkylamino, acylated amino having up to 10 carbon atoms, hydroxy, lower alkanoyloxy, oxa-lower alkoxy, lower alkoxy that is unsubstituted or substituted by carboxy, lower alkoxycarbonyl, carbamoyl or by N-lower alkylcarbamoyl, or lower alkyl that is unsubstituted or substituted by amino or by hydroxy, it being possible when several phenyl substituents $R_2$ are present for those substituents to be identical or different from one another,
$R_5$ is hydrogen or methyl, and
$R_6$ is alkoxy having from 1 to 3 carbon atoms or is nitro.

The invention relates also to compounds of formula XVIII

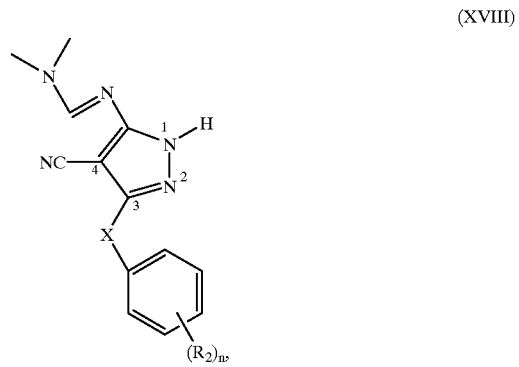

(XVIII)

wherein n is an integer from 0 up to and including 3,
X is the group $NH(CH-R_7)_t$ wherein t is an integer from 0 up to and including 3 and $R_7$ is hydrogen or lower alkyl, or the group $(C[R_3]-R_4)_q$ wherein q is an integer from 0 up to and including 3, $R_3$ is hydrogen or lower alkyl and $R_4$ is hydrogen or lower alkyl, and
$R_2$ is halogen, nitro, cyano, trifluoromethyl, carboxy, lower alkoxycarbonyl, carbamoyl, N-lower alkylcarbamoyl, N,N-di-lower alkylcarbamoyl, azido, amino, lower alkylamino, di-lower alkylamino, di-lower alkylamino-lower alkyleneamino, benzylamino; acylated or sulfonated amino each having up to 10 carbon atoms; hydroxy, lower alkanoyloxy, oxa-lower alkoxy, lower alkoxy that is unsubstituted or substituted by carboxy, lower alkoxycarbonyl, carbamoyl or by N-lower alkylcarbamoyl, or lower alkyl that is unsubstituted or substituted by amino, lower alkanoylamino, benzoylamino, lower alkoxycarbonylamino, sulfonated amino, cyano, hydroxy, lower alkanoyloxy, lower alkoxycarbonyloxy or by lower alkoxy, it being possible when several phenyl substituents $R_2$ are present for those substituents to be identical or different from one another and for two vicinal radicals $R_2$ together also to form methylenedioxy,
and to salts of such compounds having at least one salt-forming group.

The invention relates also to a method of treating warm-blooded animals suffering from a tumor disease, which method comprises administering to warm-blooded animals requiring such treatment an effective tumor-inhibiting amount of a compound of formula I or of a pharmaceutically acceptable salt thereof. The invention relates also to the use of a compound of formula I or of a pharmaceutically acceptable salt thereof for inhibiting EGF-receptor-specific protein tyrosine kinase C in warm-blooded animals or in the preparation of pharmaceutical compositions for use in the therapeutic treatment of the human or animal body. In such a treatment, a warm-blooded animal of approximately 70 kg body weight will receive effective doses that depend on species, age, individual conditions, mode of administration and individual symptoms, for example daily doses of approximately from 5 to 5000 mg, especially from 200 to 2000 mg.

The invention relates also to pharmaceutical compositions that comprise an effective amount of active ingredient, especially an amount that is effective in the prophylaxis or treatment of one of the above-mentioned diseases, together with pharmaceutically acceptable carriers that are suitable for topical, enteral, for example oral or rectal, or parenteral administration and that may be inorganic or organic, solid or liquid. There are used for oral administration especially tablets or gelatin capsules that comprise the active ingredient together with diluents, for example lactose, dextrose, sucrose, mannitol, sorbitol, cellulose and/or glycerol, and/or lubricants, for example siliceous earth, talc, stearic acid or salts thereof, such as magnesium or calcium stearate, and/or polyethylene glycol. Tablets can also comprise binders, for example magnesium aluminum silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, for example sodium alginate, and/or effervescent mixtures, or adsorbents, colorings, flavorings and sweeteners. The pharmacologically active compounds of the present invention can also be used in the form of parenterally administrable compositions or in the form of infusion solutions. Such solutions are preferably isotonic aqueous solutions or suspensions which, for example in the case of lyophilized compositions that comprise the active ingredient on its own or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating the osmotic pressure and/or buffers. The pharmaceutical compositions in question, which, if desired, may comprise further pharmacologically active substances, such as antibiotics, are prepared in a manner known per se, for example by means of conventional mixing, granulating, confectioning, dissolving or lyophilizing processes, and comprise from approximately 0.1% to 100%, especially from approximately 5% to approximately 90%, active ingredient or ingredients.

The Examples that follow illustrate the invention without limiting the invention in any way. The ratio of solvents or eluants in the solvent or eluant mixtures used is given in parts by volume (v/v) and temperatures are given in degrees Celsius.

Abbreviations:
abs.: absolute
APCI-MS: atmospheric pressure chemical ionisation mass spectrum
BOC: tert. butoxycarbonyl
DIPE: diisopropyl ether
DMEU: 1,3-dimethyl-2-imidazolidinone
DMF: dimethylformamide
EI-MS: electron impact ionization-mass spectroscopy
FAB-MS: fast atom bombardment-mass spectroscopy
HV: high vacuum
conc.: concentrated
min: minute(s)
RF: reflux
RT: room temperature
RV: rotary evaporator
brine: saturated sodium chloride solution
THF: tetrahydrofuran
TLC: thin layer chromatography
HPLC gradients:

| | |
|---|---|
| $Grad_{20-100}$ | 20% → 100% a) in b) for 20 min. |
| $Grad_{5-40}$ | 5% → 40% a) in b) for 20 min. |

Eluant a): acetonitrile +0.05% TFA; eluant b): water +0.05% TFA. Column (250×4.6 mm) filled with reversed-phase material C18-Nucleosil (5 m average particle size, silica gel covalently derivatized with octadecylsilanes, Macherey & Nagel, Düren, Germany). Detection by UV absorption at 254 nm. The retention times ($t_{Ret}$) are given in minutes. Flow rate: 1 ml/min.

EXAMPLE 1

With the exclusion of air and moisture, there is added to a suspension of 203 mg of $AlCl_3$ in 2.5 ml of absolute benzene a solution of 100 mg of 1-benzyl-3,4-diphenylamino-pyrazolo[3,4-d]pyrimidine in 2.5 ml of absolute benzene. The reaction mixture is stirred for 1.5–2 hours at 50° C. until, according to thin-layer chromatography, no starting material remains and is then stirred in approx. 30 ml of water. The precipitate is filtered off and dissolved in ethyl acetate. The ethyl acetate phase is washed several times with 5% aqueous sodium hydrogen carbonate solution and then with saturated sodium chloride solution, dried and concentrated to dryness by evaporation. The residue is crystallized from ethyl acetate/hexane, yielding 3,4-diphenylamino-1H-pyrazolo[3,4-d]pyrimidine in the form of colorless crystals, m.p. 263–264° C., FAB-MS: $(M+H)^+$=303 ($C_{17}H_{14}N_6$).

The starting material is obtained as follows:
Step 1.1:
With ice-cooling, 19.3 ml of a 5.4N sodium methanolate solution in 20 ml of methanol (purissimum) are added to 9.9 g of benzylhydrazine dihydrochloride in 20 ml of methanol (purissimum) and the reaction mixture is stirred for approx. 15 minutes at room temperature and then introduced into a solution of 4.65 g of 2-cyano-3-methylmercapto-3-phenylamino-acrylonitrile in 150 ml of absolute ethanol. The mixture is heated under reflux for approx. 17 hours and cooled to room temperature and insoluble material is filtered off with suction. The filtrate is concentrated by evaporation using a rotary evaporator and the brown oily residue is chromatographed on 190 g of silica gel, methylene chloride/ethyl acetate mixtures being used as eluant. 5-Amino-1-benzyl-4-cyano-3-phenylamino-pyrazole is obtained; m.p. 139–140° C., FAB-MS: $(M+H)^+$=290 ($C_{17}H_{15}N_5$).

Step 1.2:
1 g of 5-amino-1-benzyl-4-cyano-3-phenylamino-pyrazole and 6 ml of 85% aqueous formic acid are heated under reflux for 12 hours and then cooled to room temperature. The suspension is stirred with 20 ml of ethanol and the crude product is filtered off with suction, made into a slurry with water and again filtered off with suction. Recrystallized from tetrahydrofuran/cyclohexane yields crystalline 1-benzyl-4-hydroxy-3-phenylamino-pyrazolo[3,4-d] pyrimidine; m.p. 246–247° C., FAB-MS: $(M+H)^+$=318 ($C_{18}H_{15}N_5O$).

Step 1.3:
Under argon, 200 mg of 1-benzyl-4-hydroxy-3-phenylamino-pyrazolo[3,4-d]-pyrimidine are heated under reflux for 5 hours with 2 ml of POCl$_3$, during which time the suspension slowly becomes a solution. The light-brown solution is cooled to room temperature, concentrated to dryness by evaporation and stirred with ice-water. The crude product is filtered off with suction and recrystallized from ethanol/water, yielding fine needles of 1-benzyl-4-chloro-3-phenylamino-pyrazolo[3,4-d]pyrimidine; m.p. 135° C., FAB-MS: (M+H)$^+$=336 (C$_{18}$H$_{14}$ClN$_5$).

Step 1.4:

1 g of 1-benzyl-4-chloro-3-phenylamino-pyrazolo[3,4-d] pyrimidine is suspended in 8 ml of ethanol; 27 ml of aniline are added thereto and, under nitrogen, the reaction mixture is heated under reflux for 2.5 hours until, according to thin-layer chromatography, all the starting material has disappeared. The reaction mixture is concentrated to dryness by evaporation, the residue is suspended in water and the pH is adjusted to pH 8.5–9 with 0.1N NaOH. Extraction is then carried out with ethyl acetate and the ethyl acetate phase is then dried and concentrated by evaporation. The crude product is chromatographed on silica gel, mixtures of toluene/ethyl acetate being used as eluant. Product-containing column fractions are stirred with cyclohexane/hexane, yielding colorless crystals of 1-benzyl-3,4-diphenylamino-pyrazolo[3,4-d]pyrimidine; FAB-MS: (M+H)$^+$=393 (C$_{24}$H$_{20}$N$_6$).

EXAMPLE 2

In a manner analogous to that described in Example 1, there is obtained from 1-benzyl-3-(3-chloro-phenylamino)-4-phenylamino-pyrazolo[3,4-d]pyrimidine, by removal of the benzyl protecting group in AlCl$_3$/benzene, 3-(3-chloro-phenylamino)-4-phenylamino-1H-pyrazolo[3,4-d]pyrimidine; m.p. 230° C., FAB-MS: (M+H)$^+$=337 (C$_{17}$H$_{13}$ClN$_6$).

The starting material is obtained as follows:

Step 2.1:

Analogously to Step 1.1, there is obtained from 3-(3-chloro-phenylamino)-2-cyano-3-methylmercapto-acrylonitrile and benzylhydrazine dihydrochloride 5-amino-1-benzyl-3-(3-chloro-phenylamino)-4-cyano-pyrazole; m.p. 146–148° C.; FAB-MS: (M+H)$^+$=324 (C$_{17}$H$_{14}$ClN$_5$).

Step 2.2:

Analogously to Step 1.2, there is obtained from 5-amino-1-benzyl-3-(3-chloro-phenylamino)-4-cyano-pyrazole, by boiling with formic acid, 1-benzyl-3-(3-chloro-phenylamino)-4-hydroxy-pyrazolo[3,4-d]pyrimidine; m.p. 234–236° C., FAB-MS: (M+H)$^+$=352 (C$_{18}$H$_{14}$ClN$_5$O).

Step 2.3:

Analogously to Step 1.3, there is obtained from 1-benzyl-3-(3-chloro-phenylamino)-4-hydroxy-pyrazolo[3,4-d]pyrimidine, by boiling for 7 hours in POCl$_3$ and crystallization from ethanol, 1-benzyl-4-chloro-3-(3-chloro-phenylamino)-pyrazolo[3,4-d]pyrimidine; m.p. 148–150° C., FAB-MS: (M+H)$^+$=370 (C$_{18}$H$_{13}$Cl$_2$N$_5$).

Step 2.4:

Analogously to Step 1.4, there is obtained from 1-benzyl-4-chloro-3-(3-chloro-phenylamino)-pyrazolo[3,4-d]pyrimidine and aniline, by boiling in ethanol, 1-benzyl-3-(3-chloro-phenylamino)-4-phenylamino-pyrazolo[3,4-d]pyrimidine; m.p. 64–65° C.; FAB-MS: (M+H)$^+$=427 (C$_{24}$H$_{19}$ClN$_6$).

EXAMPLE 3

Analogously to Example 1, there is obtained from 1-benzyl-3,4-di(3-chloro-phenylamino)pyrazolo[3,4-d] pyrimidine, by removal of the benzyl protecting group in AlCl$_3$/benzene, 3,4-di(3-chloro-phenylamino)-1H-pyrazolo[3,4-d]pyrimidine; m.p. 175° C., FAB-MS: (M+H)$^+$=371 (C$_{17}$H$_{12}$Cl$_2$N$_6$).

The starting material is obtained as follows:

Step 3.1:

Analogously to Step 1.4, there is obtained from 1-benzyl-4-chloro-3-(3-chloro-phenylamino)-pyrazolo[3,4-d] pyrimidine (see Step 2.3) and 3-chloro-aniline, by boiling in ethanol, 1-benzyl-3,4-di(3-chloro-phenylamino)pyrazolo[3, 4-d]pyrimidine; m.p. 131–133° C., FAB-MS: (M+H)$^+$=461 (C$_{24}$H$_{18}$Cl$_2$N$_6$).

EXAMPLE 4

Analogously to Example 1, there is obtained from 1-benzyl-4-(3-bromo-phenylamino)-3-(3-chloro-phenylamino)-pyrazolo[3,4-d]pyrimidine, by removal of the benzyl protecting group in AlCl$_3$benzene, 4-(3-bromo-phenylamino)-3-(3-chloro-phenylamino)-1H-pyrazolo[3,4-d]pyrimidine; m.p. 179–181° C., FAB-MS: (M+H)$^+$=415 (C$_{17}$H$_{12}$BrClN$_6$).

The starting material is obtained as follows:

Step 4.1:

Analogously to Step 1.4, there is obtained from 1-benzyl-4-chloro-3-(3-chloro-phenylamino)-pyrazolo[3,4-d] pyrimidine (see Step 2.3) and 3-bromo-aniline, by boiling in ethanol, 1-benzyl-4-(3-bromo-phenylamino)-3-(3-chloro-phenylamino)-pyrazolo[3,4-d]-pyrimidine; FAB-MS: (M+H)$^+$=506 (C$_{24}$H$_{18}$ClBrN$_6$).

EXAMPLE 5

Analogously to Example 1, there is obtained from 1-benzyl-3-(3-chloro-phenylamino)-4-(3-methyl-phenylamino)-pyrazolo[3,4-d]pyrimidine, by removal of the benzyl protecting group in AlCl$_3$/benzene, 3-(3-chloro-phenylamino)-4-(3-methyl-phenylamino)-1H-pyrazolo[3,4-d]pyrimidine; m.p. 194–195° C., FAB-MS: (M+H)$^+$=351 (C$_{18}$H$_{15}$ClN$_6$).

The starting material is obtained as follows:

Step 5.1:

Analogously to Step 1.4, there is obtained from 1-benzyl-4-chloro-3-(3-chloro-phenylamino)-pyrazolo[3,4-d] pyrimidine (see Step 2.3) and 3-methyl-aniline, by boiling in ethanol, 1-benzyl-3-(3-chloro-phenylamino)-4-(3-methyl-phenylamino)-pyrazolo[3,4-d]-pyrimidine; FAB-MS: (M+H)$^+$=441 (C$_{25}$H$_{21}$ClN$_6$).

EXAMPLE 6

Analogously to Example 1, there is obtained from 1-benzyl-4-(3-[2-cyano-ethyl]-phenylamino)-3-phenylamino-pyrazolo[3,4-d]pyrimidine, by removal of the benzyl protecting group in AlCl$_3$/benzene, 4-(3-[2-cyano-ethyl]-phenylamino)-3-phenylamino-1H-pyrazolo-[3,4-d] pyrimidine; m.p. 202° C., FAB-MS: (M+H)$^+$=356 (C$_{20}$H$_{17}$N$_7$).

The starting material is obtained as follows:

Step 6.1:

Analogously to Step 1.4, there is obtained from 1-benzyl-4-chloro-3-phenylamino-pyrazolo[3,4-d]pyrimidine (see Step 1.3) and 3-[2-cyano-ethyl]-aniline, by boiling in ethanol, 1-benzyl-4-(3-[2-cyano-ethyl]-phenylamino)-3-phenylamino-pyrazolo[3,4-d]pyrimidine; FAB-MS: (M+H)$^+$=446 (C$_{27}$H$_{23}$N$_7$).

EXAMPLE 7

Analogously to Example 1, there is obtained from 1-benzyl-4-(4-[2-cyano-ethyl]-phenylamino)-3- phenylamino-pyrazolo[3,4-d]pyrimidine, by removal of the benzyl protecting group in AlCl$_3$/benzene, 4-(4-[2-cyano-ethyl]-phenylamino)-3-phenylamino-1H-pyrazolo-[3,4-d]pyrimidine; m.p. 268° C.; FAB-MS: (M+H)$^+$=356 (C$_{20}$H$_{17}$N$_7$).

The starting material is obtained as follows:
Step 7.1:
Analogously to Step 1.4, there is obtained from 1-benzyl-4-chloro-3-phenylamino-pyrazolo[3,4-d]pyrimidine (see Step 1.3) and 4-[2-cyano-ethyl]-aniline, by boiling in ethanol, 1-benzyl-4-(4-[2-cyano-ethyl]-phenylamino)-3-phenylamino-pyrazolo[3,4-d]pyrimidine; FAB-MS: (M+H)$^+$=446 (C$_{27}$H$_{23}$N$_7$).

EXAMPLE 8

Analogously to Example 1, there is obtained from 1-benzyl-4-(3-cyanomethyl-phenylamino)-3-phenylamino-pyrazolo[3,4-d]pyrimidine, by removal of the benzyl protecting group in AlCl$_3$/benzene, 4-(3-cyanomethyl-phenylamino)-3-phenylamino-1H-pyrazolo[3,4-d]-pyrimidine.

The starting material is obtained as follows:
Step 8.1:
Analogously to Step 1.4, there is obtained from 1-benzyl-4-chloro-3-phenylamino-pyrazolo[3,4-d]pyrimidine (see Step 1.3) and 3-cyanomethyl-aniline, by boiling in ethanol, 1-benzyl-4-(3-cyanomethyl-phenylamino)-3-phenylamino-pyrazolo[3,4-d]pyrimidine; m.p. 80° C., FAB-MS: (M+H)$^+$= 432 (C$_{26}$H$_{21}$N$_7$).

EXAMPLE 9

1.3 g of 3-(3-chloro-phenylamino)-4-(3-methyl-phenylamino)-1H-pyrazolo[3,4-d]-pyrimidine (see Example 5) are dissolved in 70 ml of ethanol and at room temperature 2 ml of a 4N solution of hydrogen chloride in ethanol are added thereto. After approximately 10 minutes' stirring, the HCl salt begins to crystallize out. The solution is cooled to 0° C. and the salt is crystallized out completely by the addition of ethyl ether, yielding colorless crystals of 3-(3-chloro-phenylamino)-4-(3-methyl-phenylamino)-1H-pyrazolo[3,4-d]pyrimidine hydrochloride; m.p. 260–263° C.

EXAMPLE 10

100 mg of 4-(3-[2-cyano-ethyl]-phenylamino)-3-phenylamino-1H-pyrazolo-[3,4-d]pyrimidine (see Example 6) are dissolved in 2.5 ml of absolute tetrahydrofuran and added dropwise in the course of 10 minutes to a suspension of 135 mg of aluminum trichloride in 2.5 ml of tetrahydrofuran and 46 mg of lithium aluminum hydride. The reaction is slightly exothermic. The reaction mixture is heated for 2.5 hours under reflux until, according to thin-layer chromatography, no starting material remains. The solution is cooled to 0° C., 5 ml of water are added thereto and stirring is carried out for 2 hours at room temperature. The pH is then adjusted to pH 9 with 1N sodium hydroxide solution, insoluble material is filtered off and the filtrate is concentrated by evaporation. The residue is digested in tetrahydrofuran. Again, insoluble material is filtered off. The tetrahydrofuran filtrate is concentrated to approximately 3 ml and approx. 15 ml of methylene chloride are added thereto. 5 ml of hexane are added and at 0° C. crystals of 4-(3-[3-amino-propyl]-phenylamino)-3-phenylamino-1H-pyrazolo[3,4-d]pyrimidine precipitate.

EXAMPLE 11

There is obtained from 4-(4-[2-cyano-ethyl]-phenylamino)-3-phenylamino-1H-pyrazolo[3,4-d] pyrimidine (see Example 7), by reduction with Raney nickel in a solution of ammonia in methanol and subsequent treatment with hydrogen chloride in ethanol, 4-(4-[3-amino-propyl]-phenylamino)-3-phenylamino-1H-pyrazolo[3,4-d] pyrimidine hydrochloride.

EXAMPLE 12

There is obtained from 4-(3-cyanomethyl-phenylamino)-3-phenylamino-1H-pyrazolo[3,4-d]pyrimidine (see Example 8), by reduction with Raney nickel in a solution of ammonia in methanol, 4-(3-[2-amino-ethyl]-phenylamino)-3-phenylamino-1H-pyrazolo[3,4-d]pyrimidine.

EXAMPLE 13

The following compounds of formula I are obtained analogously to the methods described in this text, for example analogously to Examples 1–3:
a) 3-(4-chloro-phenylamino)-4-(3-chloro-phenylamino)-1H-pyrazolo[3,4-d]pyrimidine,
b) 4-(3-chloro-phenylamino)-3-(3-fluoro-phenylamino)-1H-pyrazolo[3,4-d]pyrimidine,
c) 4-(3-chloro-phenylamino)-3-(4-fluoro-phenylamino)-1H-pyrazolo[3,4-d]pyrimidine,
d) 4-(3-chloro-phenylamino)-3-(4-methoxy-phenylamino)-1H-pyrazolo[3,4-d]pyrimidine,
e) 4-(3-chloro-phenylamino)-3-(4-hydroxy-phenylamino)-1H-pyrazolo[3,4-d]pyrimidine and
f) 4-(3-chloro-phenylamino)-3-(4-iodo-phenylamino)-1H-pyrazolo[3,4-d]pyrimidine, for example starting from the following compounds of formula V:
aa) Analogously to Step 1.1, there is obtained from 3-(4-chloro-phenylamino)-2-cyano-3-methylmercapto-acrylonitrile and benzylhydrazine dihydrochloride 5-amino-1-benzyl-3-(4-chloro-phenylamino)-4-cyano-pyrazole; m.p. 163–164° C., FAB-MS (M+H)$^+$: 324 (C$_{17}$H$_{14}$ClN$_5$).
ba) Analogously to Step 1.1, there is obtained from 2-cyano-3-(3-fluoro-phenylamino)-3-methylmercapto acrylonitrile and benzylhydrazine dihydrochoride 5-amino-1-benzyl-4-cyano-3-(3-fluoro-phenylamino)-pyrazole; m.p. 151–152° C., FAB-MS (M+H)$^+$: 308 (C$_{17}$H$_{14}$FN$_5$).
ca) Analogously to Step 1.1, there is obtained from 2-cyano-3-(4-fluoro-phenylamino)-3-methylmercapto-acrylonitrile and benzylhydrazine dihydrochloride 5-amino-1-benzyl-4-cyano-3-(4-fluoro-phenylamino)-pyrazole; m.p. 167–168° C., FAB-MS (M+H)$^+$: 308 (C$_{17}$H$_{14}$FN$_5$).
da) Analogously to Step 1.1, there is obtained from 2-cyano-3-(4-methoxy-phenylamino)-3-methylmercapto-acrylonitrile and benzylhydrazine dihydrochloride 5-amino-1-benzyl-4-cyano-3-(4-methoxy-phenylamino)-pyrazole; yellow resin, TLC: R$_f$=0.30 (acetic acid ethylate/hexane 1:1).
ea) Analogously to Step 1.1, there is obtained from 2-cyano-3-(4-iodo-phenylamino)-3-methylmercapto-acrylonitrile and benzylhydrazine dihydrochloride 5-amino-1-benzyl-4-cyano-3-(4-iodo-phenylamino)-pyrazole; FAB-MS (M+H)$^+$: 416 (C$_{17}$H$_{14}$IN$_5$).

EXAMPLE 14

With the exclusion of moisture, 79.2 g (295 mmol) of N'-(3-benzylamino-4-cyano-1H-pyrazol-5-yl)-N,N-dimethylformamidine are suspended in 700 ml of methanol;

60.6 g (369 mmol) of 3-chloro-aniline hydrochloride are added and the reaction mixture is boiled under reflux for 22 hours. The resulting yellow reaction solution is cooled to ≈50° C. and poured onto 2 liters of ice-water, 200 ml of saturated NaHCO$_3$ solution and 1 liter of ethyl acetate. The aqueous phase is separated off and extracted twice with ethyl acetate. The organic phases are washed twice with water, saturated NaHCO$_3$ solution, water and brine, dried (Na$_2$SO$_4$) and concentrated by evaporation to a residual volume of ≈1.5 liters. Inoculation and dilution with 300 ml of diethyl ether yield crystalline 3-benzylamino-4-(3-chloro-phenylamino)-1H-pyrazolo[3,4-d]pyrimidine; m.p. 214–217° C.; TLC: R$_f$=0.29 (ethyl acetate:hexane=1:1).

The starting material is prepared as follows:

Step 14.1:

43.6 ml (400 mmol) of benzylamine are added to a suspension of 68.4 g (400 mmol) of 3,3-bis-methylmercapto-2-cyano-acrylonitrile [3,3-bis (methylsulfanyl)-2-cyano-acrylonitrile] (Maybridge) in 400 ml of ethyl acetate. The clear solution is heated slowly to 70° C. (→ evolution of MeSH!), stirred at that temperature for 1.5 hours, cooled to RT and concentrated by evaporation, yielding crystalline 3-benzylamino-3-methylmercapto-2-cyano-acrylonitrile; $^1$H-NMR: (CD$_3$OD) 7.36 (m, 5H), 4.77 (s, 2H), 2.59 (s, 3H).

Step 14.2:

24 ml (0.48 mol) of hydrazine hydrate are added dropwise to a solution of 92 g (0.4 mol) of 3-benzylamino-3-methylmercapto-2-cyano-acrylonitrile in 400 ml of methanol, during which the temperature rises to 40° C. The reaction mixture is heated slowly to boiling (→ evolution of MeSH!), boiled for 2 hours, cooled to RT and concentrated by evaporation to a residual volume of ≈200 ml. Dilution with diethyl ether, filtering and washing with diethyl ether yield 5-amino-3-benzylamino-1H-pyrazole-4-carbonitrile [Spectrochimica Acta, 47A, 1635 (1991)]; m.p. 150–152° C.; TLC: R$_f$=0.41 (ethyl acetate).

Step 14.3:

Under a N$_2$ atmosphere, a suspension of 74.3 g (348 mmol) of 5-amino-3-benzylamino-1H-pyrazole-4-carbonitrile in 1.0 liter of toluene is boiled under reflux for 2 hours with 70.1 ml (95%; 409 mmol) of N,N-dimethylformamide diethyl acetal. Cooling to RT, filtering with suction and washing with diethyl ether yield N'-(3-benzylamino-4-cyano-1H-pyrazol-5-yl)-N,N-dimethylformamidine; m.p. 197–200° C.; TLC: R$_f$=0.50 (ethyl acetate).

Step 14.4:

60 g (0.47 mol) of 3-chloro-aniline are dissolved in 255 ml (0.56 mol) of a 2.2N solution of HCl in methanol. Concentration and stirring of the residue in diethyl ether, followed by filtering and drying, yield 3-chloro-aniline hydrochloride.

EXAMPLE 15

788 mg (4.8 mmol) of 4-formyl-benzoic acid methyl ester and 300 mg of 5% Pt/C are added to a solution of 1.04 g (4.0 mmol) of 3-amino-4-(3-chloro-phenylamino)-1H-pyrazolo[3,4-d]pyrimidine in 40 ml of DMEU and 961 mg (16 mmol) of acetic acid and hydrogenation is carried out immediately (instead of hydrogenation, reduction with NaCNBH$_3$ is also possible). After two days and after four days, a further 788 mg of 4-formylbenzoic acid methyl ester is added. After 7 days the catalyst is separated off from the reaction mixture by filtration through Celite, the filtrate is decolorized by treatment with activated carbon and then concentrated by evaporation under a high vacuum at 70° C. to give a residue of ≈4 g. Crystallization with diisopropyl ether/toluene yields product of ≈80% purity. Heating in a mixture of 30 ml of ethanol and ≈5 ml of acetone, filtering while hot, concentration by evaporation to half the volume and cooling yield 4-(3-chloro-phenylamino)-3-(4-methoxy-carbonylbenzylamino)-1H-pyrazolo[3,4-d]pyrimidine; m.p. 228° C.; FAB-MS: (M+H)$^+$=409.

The starting material is obtained as follows:

Step 15.1:

In order to remove residual water, some solvent is distilled off from a suspension of 75.8 g (216 mmol) of 3-benzylamino-4-(3-chloro-phenylamino)-1H-pyrazolo[3,4-d]-pyrimidine in 1.5 liters of benzene. Then, with exclusion of moisture, the suspension is introduced into 84 g of aluminum chloride (Fluka, Buchs/Switzerland) in 500 ml of benzene. The reaction mixture is heated at 80° C. for 2.5 hours and then cooled to RT. The supernatant benzene phase is poured into 2 kg of ice-water (leaving behind a green, oily residue) and the solid that precipitates is filtered with suction and rinsed thoroughly with water (→K$_1$). Using a rotary evaporator, the benzene is evaporated off from the filtrate, and the aqueous phase that remains is added, together with 1 kg of ice, to the green, oily residue and hydrolysis is carried out for 2 hours at 40° C. The crystalline product is filtered with suction and rinsed with water (→K$_2$). K$_1$ and K$_2$ are taken up in 1 liter of methanol, acidified with 4N aqueous HCl and partially concentrated by evaporation. Water is added and the methanol is evaporated off completely. The crystals are filtered off and rinsed with water. The same purification procedure is repeated with semi-saturated Na$_2$CO$_3$ solution/methanol and water/methanol. Stirring at 50° C. in methanol, precipitation with diethyl ether, filtering and drying yield 3-amino-4-(3-chloro-phenylamino)-1H-pyrazolo[3,4-d]pyrimidine; m.p. 232–234° C.; TLC: R$_f$=0.50 (ethyl acetate).

EXAMPLE 16

16.5 mg (0.39 mmol) of LiOH×H$_2$O are added to a mixture of 98 mg (0.24 mmol) of 3-(4-methoxycarbonylbenzylamino)-4-(3-chloro-phenylamino)-1H-pyrazolo[3,4-d]pyrimidine in 8 ml of methanol and 4 ml of water and the reaction mixture is stirred for 3 days at 45° C. The reaction mixture is concentrated by evaporation and the residue is taken up in ethanol. After the addition of activated carbon, the reaction mixture is filtered until clear and then concentrated by evaporation again. Precipitation from a solution in DMF with diethyl ether yields the lithium salt of 3-(4-carboxy-benzylamino)-4-(3-chloro-phenylamino)-1H-pyrazolo[3,4-d]pyrimidine; HPLC: T$_{Ret}$ (Grad$_{20-100}$)=9.7; FAB-MS: (M+H, acid)$^+$=395, (M+Li)$^+$=401.

EXAMPLE 17

A solution of 261 mg (1.0 mmol) of 3-amino-4-(3-chloro-phenylamino)-1H-pyrazolo[3,4-d]pyrimidine (see Step 15.1) and 245 mg (1.5 mmol) of 3-(methylamino-carbonyl)-benzaldehyde in 26 ml of methanol, 26 ml of DMEU and 180 mg (3.0 mmol) of acetic acid is stirred for 1 hour at RT. Then 440 mg (7.0 mmol) of NaCNBH$_3$ are added and the reaction mixture is stirred for 9 days at RT. The methanol is evaporated off from the reaction solution using a rotary evaporator, the residue is poured into 0.6 liter of water and stirring is carried out overnight. The product precipitates. Filtering with suction, washing with water, stirring twice in 10 ml of boiling ethanol, cooling and filtering yield 4-(3-chloro-phenylamino)-3-[3-(methylaminocarbonyl)- benzylamino]-1H-pyrazolo[3,4-d]pyrimidine; m.p. 252–254° C.; HPLC: $T_{Ret}(Grad_{5-40})$=16.9; FAB-MS: $(M+H)^+$=408.

The starting material is prepared as follows:
Step 17.1:

A solution of 3 g of 3-formyl-benzoic acid methyl ester and 20 ml of methylamine (8.03M in ethanol) is stirred for 3 days at RT. Concentration by evaporation and crystallization from DIPE yield N-methyl-3-methyliminomethyl-benzamide; m.p. 87° C.
Step 17.2:

A two-phase mixture of 2.91 g of N-methyl-3-methyliminomethyl-benzamide, 50 ml of methylene chloride and 30 ml of 1N HCl is stirred for 1.5 hours at RT. Separating off the organic phase, washing with 1N HCl and brine, drying with $Na_2SO_4$, concentrating by evaporation and stirring with DIPE/hexane yield 3-(methylaminocarbonyl)-benzaldehyde; m.p. 101–102° C.

EXAMPLE 18

Analogously to Example 17, there is prepared from 261 mg (1.0 mmol) of 3-amino-4-(3-chloro-phenylamino)-1H-pyrazolo[3,4-d]pyrimidine (see Step 15.1) and 245 mg (1.5 mmol) of 4-(methylaminocarbonyl)-benzaldehyde, 4-(3-chloro-phenylamino)-3-[4-(methylaminocarbonyl)-benzylamino]-1H-pyrazolo[3,4-d]pyrimidine; HPLC: $T_{Ret}$ $(Grad_{5-40})$=16.3; $^1$H-NMR: (DMSO-$d_6$) 12.38 (s, HN), 8.93 (s, HN), 8.39 (m, 1H), 8.27 (s, 1H), 7.94 (t, J=2, 1H), 7.81 (d, J=8, 2H), 7.68 (db, J=8, 1H), 7.52 (d, J=8, 2H), 7.41 (t, J=8, 1H), 7.17 (db, J=8, 1H), 6.99 (tb, J=5, HN), 4.57 (d, J=5, 2H), 2.79 (d, J=4, 3H); FAB-MS: $(M+H)^+$=408.

The starting material is prepared analogously to Steps 17.1 and 17.2:
Step 18.1:

There is obtained from 3 g of 4-formyl-benzoic acid methyl ester and 20 ml of methylamine (8.03M in ethanol) N-methyl-4-methyliminomethyl-benzamide; m.p. 140–141° C.
Step 18.2:

705 mg of N-methyl-4-methyliminomethyl-benzamide are hydrolyzed to form 3-(methylaminocarbonyl)-benzaldehyde; $^1$H-NMR: (CDCl$_3$) 10.06 (s, 1H), 7.93 (s, 4H), 6.4 (sb, HN), 3.04 (d, J=5, 3H).

EXAMPLE 19

99.7 mg (0.60 mmol) of 3,5-dimethoxy-benzaldehyde are added to a solution of 130 mg (0.50 mmol) of 3-amino-4-(3-chloro-phenylamino)-1H-pyrazolo[3,4-d]pyrimidine in 26 ml of methanol and 120 mg (2.0 mmol) of acetic acid. As the reaction mixture is stirred, a solid precipitates which can be dissolved again by the addition of 52 ml of DMEU. 220 mg (3.5 mmol) of NaCNBH$_3$ are added thereto and stirring is then continued for 5 hours at RT. Since not all of the 3-amino-4-(3-chloro-phenylamino)-1H-pyrazolo[3,4-d] pyrimidine has been reacted (HPLC), 220 mg of NaCNBH$_3$ are added twice more and stirring is continued for 5 hours each time. The reaction solution is then poured into 1 liter of water, stirred vigorously for 1 hour and filtered. Crystallization of the filtration residue from acetone yields 4-(3-chloro-phenylamino)-3-(3,5-dimethoxybenzylamino)-1H-pyrazolo[3,4-d]pyrimidine; m.p. 208–209° C.; HPLC: $T_{Ret}$ $(Grad_{20-100})$=11.7; FAB-MS: $(M+H)^+$=411.

EXAMPLE 20

228 mg (1.50 mmol) of 4-hydroxy-3-methoxy-benzaldehyde are added ($N_2$ atmosphere) to a solution of 261 mg (1.00 mmol) of 3-amino-4-(3-chloro-phenylamino)-1H-pyrazolo[3,4-d]pyrimidine in 26 ml of methanol, 26 ml of DMEU and 120 mg (2.0 mmol) of acetic acid. After 1 hour, 440 mg (7.0 mmol) of NaCNBH$_3$ are added to the clear solution and stirring is then carried out at RT for 7 days. The reaction solution is poured into 0.8 liter of water and stirred overnight to complete the reaction, during which time the product precipitates. Filtering with suction, washing with water, stirring in hot ethyl acetate, cooling and filtering yield 4-(3-chloro-phenylamino)-3-[(3-methoxy-4-hydroxy-benzyl)-amino]-1H-pyrazolo[3,4-d]pyrimidine; m.p. 223–225° C.; HPLC: $T_{Ret}(Grad_{5-40})$=19.8; FAB-MS: $(M+H)^+$=397.

EXAMPLE 21

225 mg (1.50 mmol) of 3-formyl-benzoic acid are added to a solution of 261 mg (1.00 mmol) of 3-amino-4-(3-chloro-phenylamino)-1H-pyrazolo[3,4-d]pyrimidine in 26 ml of methanol, 13 ml of DMEU and 120 mg (2.0 mmol) of acetic acid under a $N_2$ atmosphere. The reaction mixture is stirred for 1 hour, during which time a solid precipitates, and then 440 mg (7.0 mmol) of NaCNBH$_3$ are added. Stirring is carried out for 5 days, the suspension changing to a clear solution. The methanol is evaporated off using a rotary evaporator. The residue is poured into 0.6 liter of water and stirred for 3 hours to complete the reaction. Filtering with suction, washing with water and diethyl ether, stirring in hot ethanol, cooling and filtering yield 3-(3-carboxy-benzylamino)-4-(3-chloro-phenylamino)-1H-pyrazolo[3,4-d]pyrimidine (3-{[4-(3-chloro-phenylamino)-1H-pyrazolo [3,4-d]pyrimidin-3-yl-amino]methyl}-benzoic acid); m.p. 294–296° C.; HPLC: $T_{Ret}(Grad_{5-40})$=20.1; FAB-MS: $(M+H)^+$=395.

EXAMPLE 22

Analogously to Example 21, 1.00 mmol of 3-amino-4-(3-chloro-phenylamino)-1H-pyrazolo[3,4-d]pyrimidine in 26 ml of methanol, 13 ml of DMEU and 3.0 mmol of acetic acid are first reacted with 3-formyl-benzoic acid methyl ester and then reduced with 7.00 mmol of NaCNBH$_3$ (5–7 days). 4-(3-Chloro-phenylamino)-3-(3-methoxycarbonyl-benzylamino)-1H-pyrazolo[3,4-d]pyrimidine is obtained.

Preferably, the same compound is obtained as follows: To 70 mg (0.177 mmol) of 3-(3-carboxy-benzyl-amino)-4-(3-chloro-phenylamino)-1H-pyrazolo[3,4-d]pyrimidine (cf. Example 21) and 2 ml of methanol are added 0.1 ml of thionylchloride. The mixture is stirred in a sealed vessel for 3 h at 70° C., and then cooled to room temperature. Filtration and washing with methanol affords 4-(3-chloro-phenylamino)-3-(3-methoxycarbonyl-benzylamino)-1H-pyrazolo[3,4-d]pyrimidine-hydrochloride; ($C_{20}H_{17}N_6ClO_2 \times HCl \times 0.28H_2O$), calc. C 53.34, H 4.15, N 18.66, Cl 15.74, $H_2O$ 1.12, found C 53.35, H 4.13, N 18.82, Cl 15.87, $H_2O$ 1.12.

EXAMPLE 23

Analogously to Example 21, 1.00 mmol of 3-amino-4-(3-chloro-phenylamino)-1H-pyrazolo[3,4-d]pyrimidine in 26 ml of methanol, 13 ml of DMEU and 3.0 mmol of acetic acid are first reacted with 3,4,5-trimethoxy-benzaldehyde and then reduced with 7.00 mmol of NaCNBH$_3$ (5–7 days). 4-(3-Chloro-phenylamino)-3-(3,4,5-trimethoxybenzylamino)-1H-pyrazolo[3,4-d]pyrimidine is obtained; m.p. 240–245° C. HPLC: $T_{Ret}(Grad_{5-40})$=22.

EXAMPLE 24

Analogously to Example 21, 1.00 mmol of 3-amino-4-(3-chloro-phenylamino)-1H-pyrazolo[3,4-d]pyrimidine in 26 ml of methanol, 13 ml of DMEU and 3.0 mmol of acetic acid are first reacted with 3,4-dimethoxy-benzaldehyde and then reduced with 7.00 mmol of $NaCNBH_3$ (5–7 days). 4-(3-Chloro-phenylamino)-3-(3,4-dimethoxybenzylamino)-1H-pyrazolo[3,4-d]pyrimidine is obtained; m.p. 228–232° C.; $T_{Ret}(Grad_{5-40})$=19.0.

EXAMPLE 25

Analogously to Example 21, 1.00 mmol of 3-amino-4-(3-chloro-phenylamino)-1H-pyrazolo[3,4-d]pyrimidine in 26 ml of methanol, 13 ml of DMEU and 3.0 mmol of acetic acid are first reacted with 2,3,4-trimethoxy-benzaldehyde and then reduced with 7.00 mmol of $NaCNBH_3$ (5–7 days). 4-(3-Chloro-phenylamino)-3-(2,3,4-trimethoxybenzylamino)-1H-pyrazolo[3,4-d]pyrimidine is obtained; m.p. 168–169° C.; HPLC: $T_{Ret}(Grad_{5-40})$=20.2.

EXAMPLE 26

Analogously to Example 21, 1.00 mmol of 3-amino-4-(3-chloro-phenylamino)-1H-pyrazolo[3,4-d]pyrimidine in 26 ml of methanol, 13 ml of DMEU and 3.0 mmol of acetic acid are first reacted with 3-hydroxy-4-methoxy-benzaldehyde and then reduced with 7.00 mmol of $NaCNBH_3$ (5–7 days). 4-(3-Chloro-phenylamino)-3-(3-hydroxy-4-methoxy-benzylamino)-1H-pyrazolo[3,4-d]pyrimidine is obtained; m.p. 225–227° C.; HPLC: $T_{Ret}(Grad_{5-40})$=17.6.

EXAMPLE 27

Analogously to Example 21, 1.00 mmol of 3-amino-4-(3-chloro-phenylamino)-1H-pyrazolo[3,4-d]pyrimidine in 26 ml of methanol, 13 ml of DMEU and 3.0 mmol of acetic acid are first reacted with 4-hydroxy-3,5-dimethoxy-benzaldehyde and then reduced with 7.00 mmol of $NaCNBH_3$ (5–7 days). 4-(3-Chloro-phenylamino)-3-(4-hydroxy-3,5-dimethoxy-benzylamino)-1H-pyrazolo[3,4-d]pyrimidine is obtained; HPLC: $T_{Ret}(Grad_{5-40})$=17.0.

EXAMPLE 28

Analogously to Example 21, 1.00 mmol of 3-amino-4-(3-chloro-phenylamino)-1H-pyrazolo[3,4-d]pyrimidine in 26 ml of methanol, 13 ml of DMEU and 3.0 mmol of acetic acid are first reacted with 3,4-methylenedioxy-benzaldehyde and then reduced with 7.00 mmol of $NaCNBH_3$ (5–7 days). 4-(3-Chloro-phenylamino)-3-(3,4-methylenedioxybenzylamino)-1H-pyrazolo[3,4-d]pyrimidine is obtained; m.p. 220–222° C.; HPLC: $T_{Ret}(Grad_{5-40})$=22.5° C.

EXAMPLE 29

Analogously to Example 21, 1.00 mmol of 3-amino-4-(3-chloro-phenylamino)-1H-pyrazolo[3,4-d]pyrimidine in 26 ml of methanol, 13 ml of DMEU and 3.0 mmol of acetic acid are first reacted with 2,3-methylenedioxy-benzaldehyde and then reduced with 7.00 mmol of $NaCNBH_3$ (5–7 days). 4-(3-Chloro-phenylamino)-3-(2,3-methylenedioxybenzylamino)-1H-pyrazolo[3,4-d]pyrimidine is obtained; m.p. 214–215° C.; HPLC: $T_{Ret}(Grad_{5-40})$=24.1.

EXAMPLE 30

Analogously to Example 21, 1.00 mmol of 3-amino-4-(3-chloro-phenylamino)-1H-pyrazolo[3,4-d]pyrimidine in 26 ml of methanol, 13 ml of DMEU and 3.0 mmol of acetic acid are first reacted with 3-chloro-benzaldehyde and then reduced with 7.00 mmol of $NaCNBH_3$ (5–7 days). 3-(3-Chloro-benzylamino)-4-(3-chloro-phenylamino)-1H-pyrazolo-[3,4-d]pyrimidine is obtained; m.p. 158–163° C.; HPLC: $T_{Ret}(Grad_{20-100})$=12.4.

EXAMPLE 31

Analogously to Example 21, 1.00 mmol of 3-amino-4-(3-chloro-phenylamino)-1H-pyrazolo[3,4-d]pyrimidine in 26 ml of methanol, 13 ml of DMEU and 3.0 mmol of acetic acid are first reacted with 3-chloro-4-hydroxy-benzaldehyde and then reduced with 7.00 mmol of $NaCNBH_3$ (5–7 days). 3-(3-Chloro-4-hydroxy-benzylamino)-4-(3-chloro-phenylamino)-1H-pyrazolo[3,4-d]pyrimidine is obtained; m.p. 220° C.; HPLC: $T_{Ret}(Grad_{5-40})$=18.7.

EXAMPLE 32

Analogously to Example 21, 1.00 mmol of 3-amino-4-(3-chloro-phenylamino)-1H-pyrazolo[3,4-d]pyrimidine in 26 ml of methanol, 13 ml of DMEU and 3.0 mmol of acetic acid are first reacted with 3-chloro-4-methoxy-benzaldehyde and then reduced with 7.00 mmol of $NaCNBH_3$ (5–7 days). 3-(3-Chloro-4-methoxy-benzylamino)-4-(3-chloro-phenylamino)-1H-pyrazolo[3,4-d]pyrimidine is obtained; m.p. 205–208° C.; HPLC: $T_{Ret}(Grad_{20-100})$=12.2.

EXAMPLE 33

There are obtained analogously to the processes described in this text:
a) 4-(3-chloro-phenylamino)-3-{[1-(3-chloro-phenyl)-ethyl]-amino}-1H-pyrazolo[3,4-d]-pyrimidine,
b) 4-(3-chloro-phenylamino)-3-[(1-phenyl-ethyl)-amino]-1H-pyrazolo[3,4-d]pyrimidine [prepared as described in example 14, starting from (±)-1-phenyl-ethylamine and 3,3-bis-(methylmercapto)-2-cyano-acrylonitril]; $T_{Ret}(Grad_{20-100})$=11.8; FAB-MS: $(M+H)^+$=365, and
c) 4-(3-chloro-phenylamino)-3-[3-(dimethylaminocarbonyl)-benzylamino]-1H-pyrazolo[3,4-d]-pyrimidine.

EXAMPLE 34

1.31 g (7.98 mmol) of 3-chloro-aniline hydrochloride (see Step 14.4) are added to a suspension of 2.05 g (7.6 mmol) of N'-[3-(4-methoxy-phenyl)-4-cyano-1H-pyrazol-5-yl]-N,N-dimethyl-formamidine in 24 ml of methanol and the reaction mixture is boiled under reflux. After 13 hours a further 561 mg (3.42 mmol) of 3-chloro-aniline hydrochloride is added. After a total boiling time of 18 hours, the suspension is cooled. 4-(3-Chloro-phenylamino)-3-(4-methoxy-phenyl)-1H-pyrazolo[3,4-d]pyrimidine is filtered off, washed with hexane and dried: m.p. 268–269° C.; HPLC: $T_{Ret}(Grad_{20-100})$=13.8; FAB-MS: $(M+H)^+$=352.

The starting material is prepared as follows:
Step 34.1:
Under a $N_2$ atmosphere, a suspension of 1.87 g (8.16 mmol) of 5-amino-3-(4-methoxy-phenyl)-1H-pyrazole-4-carbonitrile (for preparation see: *J. Heterocyclic Chem.* 27, 647 (1990)) in 33 ml of toluene is boiled under reflux for 3.5 hours with 1.64 ml of N,N-dimethylformamide diethyl acetal (95%; 9.1 mmol). Crystallization by cooling to 0° C., filtering with suction and washing with hexane yield N'-[3-(4-methoxy-phenyl)-4-cyano-1H-pyrazol-5-yl]-N,N-dimethylformamidine; m.p. 169–171° C.; TLC: $R_f$=0.18 (ethyl acetate:hexane=1:1); MS: $(M)^+$=269.

EXAMPLE 35

With the exclusion of moisture, 62 mg (0.38 mmol) of 3-chloro-aniline hydrochloride (see Step 14.4) are added to 92 mg (0.36 mmol) of N'-[3-(4-amino-phenyl)-4-cyano-1H-pyrazol-5-yl]-N,N-dimethylformamidine in 1 ml of methanol and the reaction mixture is boiled under reflux for 28 hours. The light-yellow reaction solution is cooled, concentrated by evaporation and chromatographed ($SiO_2$, methylene chloride/ethanol [10:1]). Crystallization from isopropanol yields 3-(4-amino-phenyl)-4-(3-chloro-phenylamino)-1H-pyrazolo[3,4-d]pyrimidine; TLC: $R_f$=0.33 (methylene chloride:methanol=10:1); FAB-MS: $(M)^+$=336; HPLC: $T_{Ret}$(Grad$_{20-100}$)=9.2, $T_{Ret}$(Grad$_{5-40}$)=18.8.

As an alternative to the above method, 3-(4-amino-phenyl)-4-(3-chloro-phenylamino)-1H-pyrazolo[3,4-d]pyrimidine can also be prepared from 3-(4-tert-butoxycarbonylamino-phenyl)-4-(3-chloro-phenylamino)-1H-pyrazolo[3,4-d]pyrimidine (Example 36) by stirring for 3 hours in 4N HCl solution in dioxane and filtering off the product in the form of the hydrochloride.

The starting material is prepared as follows:

Step 35.1:

Under a $N_2$ atmosphere, 0.92 g (6.38 mmol) of tetracyanoethylene oxide (Fluka, Buchs/Switzerland) is added to 618.5 mg (2.9 mmol) of 4-nitro-dithiobenzoic acid methyl ester (for preparation see *J. prakt. Chem.* 331, 243 (1989)) in 5 ml of toluene and the reaction mixture is then boiled for 4 hours. The reaction mixture is cooled, 10 g of silica gel are added thereto and the reaction mixture is concentrated by evaporation using a rotary evaporator. Application of the residue to a silica gel column and elution with hexane/ethyl acetate (2:1) yield 3-(4-nitrophenyl)-3-methylmercapto-2-cyano-acrylonitrile; TLC: $R_f$=0.46 (ethyl acetate:hexane=1:2); MS: $(M)^+$=245.

Step 35.2:

0.05 ml (1.00 mmol) of hydrazine hydrate is added dropwise to 245.3 mg (1.00 mmol) of 3-(4-nitrophenyl)-3-methylmercapto-2-cyano-acrylonitrile in 1.3 ml of methanol and the reaction mixture is then boiled for 8 hours and then concentrated by evaporation. The residue is stirred with ethyl acetate and filtered, yielding 5-amino-3-(4-nitrophenyl)-1H-pyrazole-4-carbonitrile; TLC: $R_f$=0.14 (ethyl acetate:hexane=1:1).

Step 35.3:

In 1 ml of toluene, 57.3 mg (0.25 mmol) of 5-amino-3-(4-nitro-phenyl)-1H-pyrazole-4-carbonitrile and 79.3 μl of N,N-dimethylformamide dibenzylacetal are boiled overnight. Filtering of the suspension and washing with hexane yield N'-[3-(4-nitro-phenyl)-4-cyano-1H-pyrazol-5-yl]-N,N-dimethylformamidine; TLC: $R_f$=0.15 (ethyl acetate:hexane=2:1); $T_{Ret}$(Grad$_{20-100}$)=8.8.

Step 35.4:

In the presence of 30 mg of Pd/C (5%), 142 mg (0.50 mmol) of N'-[3-(4-nitro-phenyl)-4-cyano-1H-pyrazol-5-yl]-N,N-dimethylformamidine are hydrogenated in 20 ml of THF. Filtering, concentration by evaporation and crystallization from ethyl acetate/diethyl ether/hexane yield N'-[3-(4-amino-phenyl)-4-cyano-1H-pyrazol-5-yl]-N,N-dimethylformamidine; TLC: $R_f$=0.07 (ethyl acetate:hexane=3:1); FAB-MS: $(M+H)^+$=255.

EXAMPLE 36

With the exclusion of air, 172 mg (1.05 mmol) of 3-chloro-aniline hydrochloride (see Step 14.4) are added to 248 mg (0.70 mmol) of N'-[3-(4-tert-butoxycarbonylamino-phenyl)-4-cyano-1H-pyrazol-5-yl]-N,N-dimethylformamidine in 2 ml of methanol and the reaction mixture is boiled for 19 hours. The reaction mixture is then concentrated by evaporation and chromatographed ($SiO_2$, methylene chloride/ethanol [20:1]). Stirring with diethyl ether/hexane yields 3-(4-tert-butoxycarbonylamino-phenyl)-4-(3-chloro-phenylamino)-1H-pyrazolo[3,4-d]pyrimidine; m.p. 165–168° C. (decomposition); FAB-MS: $(M)^{+-}$=436; HPLC: $T_{Ret}$(Grad$_{20-100}$)=15.4.

The starting material is prepared as follows:

Step 36.1:

Under an argon atmosphere, 254 mg (1.0 mmol) of N'-[3-(4-amino-phenyl)-4-cyano-1H-pyrazol-5-yl]-N,N-dimethylformamidine (Step 35.4) in 4 ml of dioxane and 436.5 mg (2.0 mmol) of di-tert-butyl dicarbonate are heated at 80° C. for 7 hours. Cooling, concentration by evaporation to a residual volume of ≈1 ml, the addition of ≈2 ml of hexane and filtering yield N'-[3-(4-tert-butoxycarbonylamino-phenyl)-4-cyano-1H-pyrazol-5-yl]-N,N-dimethylformamidine; m.p. 230–233° C. (decomposition); TLC: $R_f$=0.47 (methylene chloride:methanol=10:1); MS: $(M)^+$=354.

EXAMPLE 37

With the exclusion of air, 172.2 mg (1.05 mmol) of 3-chloro-aniline hydrochloride (see Step 14.4) are added to 199 mg (0.70 mmol) of N'-[3-(3-nitro-phenyl)-4-cyano-1H-pyrazol-5-yl]-N,N-dimethylformamidine in 2 ml of methanol and the reaction mixture is boiled under reflux for 19 hours. Cooling, filtering and washing with isopropanol and hexane yield 4-(3-chloro-phenylamino)-3-(3-nitro-phenyl)-1H-pyrazolo[3,4-d]pyrimidine; TLC: Rt=0.55 (methylene chloride:methanol=10:1); HPLC: $T_{Ret}$(Grad$_{20-100}$)=14.2; $^1$H-NMR: (DMSO-$d_6$) 9.05 (s, HN), 8.54 (s, 2H), 8.32 (dd, J=8, 2, 1H), 8.22 (d, J=8, 1H), 7.8 (m, 2H), 7.49 (d, J=8, 1H), 7.33 (t, J=8, 1H), 7.10 (dd, J=8, 2, 1H).

The starting material is prepared as follows:

Step 37.1:

Under a $N_2$ atmosphere, 13.47 g (0.42 mol) of sulfur and 60.72 g of triethylamine are introduced into 65 ml of DMF. At 0–5° C., a solution of 30 g (175 mmol) of 3-nitro-benzyl chloride in 35 ml of DMF is added dropwise thereto and the reaction mixture is then stirred for 1.5 hours at 0–5° C., for 3 hours at RT and finally for 4 hours at 40° C. (→ exothermic). Then the orange reaction mixture is cooled to 0° C. and 13 ml (208 mmol) of methyl iodide are added. The red suspension is stirred overnight at 0–5° C., poured into ice-water and then stirred for 1 hour. Ethyl acetate is added and the sulfur is filtered off. The aqueous phase is separated off and extracted once with ethyl acetate. The organic phases are washed 3 times with water and brine, dried with $Na_2SO_4$ and concentrated by evaporation. Column chromatography ($SiO_2$, ethyl acetate/hexane [1:4]) and crystallization from a diethyl ether solution by the addition of hexane and cooling to –70° C. yield 3-nitro-dithiobenzoic acid methyl ester; m.p. 38° C.

Step 37.2:

Under a $N_2$ atmosphere, 550 mg (3.8 mmol) of tetracyanoethylene oxide (Fluka, Buchs/Switzerland) are added to 500 mg (2.34 mmol) of 3-nitro-dithiobenzoic acid methyl ester in 4 ml of toluene and the reaction mixture is then heated at 50° C. for 10 hours. 5 g of silica gel are added to the reaction mixture, which is then concentrated by evaporation. Application of the residue to a silica gel column, elution with hexane/ethyl acetate [1:2], treatment with activated carbon, concentration by evaporation and crystallization from diethyl ether (–70° C.) yield 3-(3-nitrophenyl)-3-methylmercapto-2-cyano-acrylonitrile; MS: $(M)^+$=245, (M-SMe)⁺=198, (M-NO₂-Me)⁺=184; IR: (KBr) 2222s, 1531s, 1514s, 1353s.

Step 37.3:

0.24 ml (4.8 mmol) of hydrazine hydrate is added dropwise to 1.00 g (4.08 mmol) of 3-(3-nitro-phenyl)-3-methylmercapto-2-cyano-acrylonitrile in 5.3 ml of methanol and the reaction mixture is then boiled for 1.5 hours. The reaction mixture is then cooled in ice-water and the precipitate is filtered off and washed with diethyl ether/isopropanol (2:1), yielding 5-amino-3-(3-nitro-phenyl)-1H-pyrazole-4-carbonitrile; TLC: $R_f$=0.4 (methylene chloride:methanol= 10:1); $T_{Ret}$(Grad$_{20-100}$)=10.8; MS: (M)⁺=229, (M-NO₂)⁺=183.

Step 37.4:

In 8 ml of toluene, 229 mg (1.00 mmol) of 5-amino-3-(3-nitro-phenyl)-1H-pyrazole-4-carbonitrile and 317 μl of N,N-dimethylformamide dibenzylacetal are boiled overnight. Cooling, filtering the suspension and washing with hexane yield N'-[3-(3-nitrophenyl)-4-cyano-1H-pyrazol-5-yl]-N,N-dimethylformamidine; m.p. 221–225° C.; $T_{Ret}$(Grad$_{22-100}$)=8.7.

EXAMPLE 38

In the presence of 30 mg of Raney nickel, 110 mg (0.30 mmol) of 3-(3-nitro-phenyl)-4-(3-chloro-phenylamino)-1H-pyrazolo[3,4-d]pyrimidine are hydrogenated in 3 ml of methanol and 3 ml of THF. The catalyst is filtered off, then 15 g of silica gel are added to the filtrate, which is then concentrated by evaporation. Application of the powder to a silica gel column, elution with methylene chloride/ethanol (15:1) and stirring of the crude product with diethyl ether/hexane yield 3-(3-amino-phenyl)-4-(3-chloro-phenylamino)-1H-pyrazolo-[3,4-d]pyrimidine; m.p. 264–266° C.; TLC: $R_f$=0.45 (methylene chloride/methanol 10:1); HPLC: $T_{Ret}$(Grad$_{20-100}$)=9.7.

EXAMPLE 39

The following compounds are obtained analogously to the processes described in this text:

a) 4-(3-chloro-phenylamino)-3-(4-[3-methyl-butanoylamino]-phenyl)-1H-pyrazolo[3,4-d]-pyrimidine, b) 4-(3-chloro-phenylamino)-3-(3-[3-methyl-butanoylamino]-phenyl)-1H-pyrazolo[3,4-d]-pyrimidine, c) 4-(3-chloro-phenylamino)-3-(4-propanoylamino-phenyl)-1H-pyrazolo[3,4-d]pyrimidine, d) 4-(3-chloro-phenylamino)-3-(3-propanoylamino-phenyl)-1H-pyrazolo[3,4-d]pyrimidine, e) 4-(3-chloro-phenylamino)-3-(4-pivaloylamino-phenyl)-1H-pyrazolo[3,4-d]pyrimidine; HPLC: $T_{Ret}$(Grad$_{20-100}$)=14.3, FAB-MS: (M+H)⁺=421 f) 4-(3-chloro-phenylamino)-3-(3-pivaloylamino-phenyl)-1H-pyrazolo[3,4-d]pyrimidine; HPLC: $T_{Ret}$(Grad$_{20-100}$)=15.06, FAB-MS: (M+H)⁺=421, g) 3-(4-acetylamino-phenyl)-4-(3-chloro-phenylamino)-1H-pyrazolo[3,4-d]pyrimidine; HPLC: $T_{Ret}$(Grad$_{20-100}$)=11.4, FAB-MS: (M+H)⁺=379, h) 3-(3-acetylamino-phenyl)-4-(3-chloro-phenylamino)-1H-pyrazolo[3,4-d]pyrimidine, HPLC: $T_{Ret}$(Grad$_{20-100}$)=12.0, FAB-MS: (M+H)⁺=379, i) 4-(3-chloro-phenylamino)-3-(4-[{N,N-dimethylamino}-methyleneamino]-phenyl)-1H-pyrazolo[3,4-d]pyrimidine, j) 4-(3-chloro-phenylamino)-3-(3-[{N,N-dimethylamino}-methyleneamino]-phenyl)-1H-pyrazolo[3,4-d]pyrimidine, k) 4-(3-chloro-phenylamino)-3-(4-[thien-2-yl-carbonylamino]-phenyl)-1H-pyrazolo[3,4-d]-pyrimidine, l) 4-(3-chloro-phenylamino)-3-(3-[thien-2-yl-carbonylamino]-phenyl)-1H-pyrazolo[3,4-d]-pyrimidine, HPLC: $T_{Ret}$(Grad$_{20-100}$)=14,3, MS: (M)⁺=421, m) 4-(3-chloro-phenylamino)-3-(4-[fur-2-yl-carbonylamino]-phenyl)-1H-pyrazolo[3,4-d]-pyrimidine, n) 4-(3-chloro-phenylamino)-3-(3-[fur-2-yl-carbonylamino]-phenyl)-1H-pyrazolo[3,4-d]-pyrimidine, o) 4-(3-chloro-phenylamino)-3-(4-[pyrid-2-yl-carbonylamino]-phenyl)-1H-pyrazolo[3,4-d]-pyrimidine, p) 4-(3-chloro-phenylamino)-3-(3-[pyrid-2-yl-carbonylamino]-phenyl)-1H-pyrazolo[3,4-d]-pyrimidine, q) 4-(3-chloro-phenylamino)-3-(4-methylsulfonylamino-phenyl)-1H-pyrazolo[3,4-d]pyrimidine, r) 4-(3-chloro-phenylamino)-3-(3-methylsulfonylamino-phenyl)-1H-pyrazolo[3,4-d]pyrimidine; HPLC: $T_{Ret}$(Grad$_{20-100}$)=12,02, FAB-MS: (M+H)⁺=415, s) 4-(3-chloro-phenylamino)-3-(4-[4-methyl-benzenesulfonylamino]-phenyl)-1H-pyrazolo-[3,4-d]pyrimidine, t) 4-(3-chloro-phenylamino)-3-(3-[4-methyl-benzenesulfonylamino]-phenyl)-1H-pyrazolo-[3,4-d]pyrimidine, u) 3-(3-tert-butoxycarbonylamino-phenyl)-4-(3-chloro-phenylamino)-1H-pyrazolo[3,4-d]-pyrimidine, v) 3-(4-benzyloxycarbonylamino-phenyl)-4-(3-chloro-phenylamino)-1H-pyrazolo[3,4-d]-pyrimidine and w) 3-(3-benzyloxycarbonylamino-phenyl)-4-(3-chloro-phenylamino)-1H-pyrazolo[3,4-d]-pyrimidine.

EXAMPLE 40

4-(3-Chloro-phenylamino)-3-(4-methoxy-phenylamino)-1H-pyrazolo[3,4-d]-pyrimidine A suspension of 1 g (3.52 mmol) of 4-cyano-5-(dimethylamino-methyleneamino)-3-(4-methoxy-phenylamino)-pyrazole and 0.9 g (5.48 mmol) of 3-chloro-aniline hydrochloride [for preparation see: Step 14.4, cf. Justus Liebigs Ann. Chem. 176, 45 (1875)] in 7 ml of methanol is heated under reflux for 17 hours. The reaction mixture is then cooled to room temperature, rendered alkaline (pH 10) by the addition of 1N sodium hydroxide solution and filtered and the filter residue is washed with a methanol/water mixture (1:1).

Recrystallization of the crude product from methanol/water yields the title compound having a water-content of 1.69% H₂O; m.p. 223–224° C. (decomp.).

The starting material is prepared as follows:

Step 40.1:

4-Cyano-5-(dimethylamino-methyleneamino)-3-(4-methoxy-phenylamino)-pyrazole

A suspension of 5.41 g (23.6 mmol) of 5-amino-4-cyano-3-(4-methoxy-phenylamino)-pyrazole [for preparation see: J. Heterocyclic Chem. 27, 775 (1990)] in 4.8 ml (27.2 mmol) of N,N-dimethylformamide diethyl acetal (97%) and 100 ml of toluene is heated under reflux for 5 hours. The reaction mixture is then cooled to room temperature and filtered and the filter residue is washed with toluene. Recrystallization of the crude product from methanol/water yields the title compound; m.p. 232–234° C. (decomp.).

EXAMPLE 41

3-(4-Acetylamino-phenylamino)-4-(3-chloro-phenylamino)-1H-pyrazolo[3,4-d]-pyrimidine A suspension of 6.32 g (20.3 mmol) of 3-(4-acetylamino-phenylamino)-4-cyano-5-(dimethylamino-methyleneamino)-pyrazole and 4 g (24.4 mmol) of 3-chloro-aniline hydrochloride in 50 ml of methanol is heated under reflux for 96 hours and then cooled to room temperature. The reaction mixture is filtered and the filter residue is digested for ½ hour in 50 ml of 1N sodium hydroxide solution. Filtering and washing with water yield the title compound; m.p. 290–291° C. (decomp.).

The starting material is prepared as follows:

Step 41.1:
3-(4-Acetylamino-phenylamino)-2-cyano-3-methylmercapto-acrylonitrile

A mixture of 5 g (29.4 mmol) of 3,3-bis-methylmercapto-2-cyano-acrylonitrile [for preparation see: Chem. Ber. 95, 2861 (1962)], 4.41 g (29.4 mmol) of 4-amino-acetanilide (Fluka) and 30 ml of toluene is heated under reflux for 20 hours. Cooling to room temperature, filtering and washing the filter residue with toluene yield the title compound; m.p 258–259° C. (decomp.).

Step 41.2:
3-(4-Acetylamino-phenylamino)-5-amino-4-cyano-pyrazole

A mixture of 7.46 g (27.4 mmol) of 3-(4-acetylamino-phenylamino)-2-cyano-3-methylmercapto-acrylonitrile, 1.63 ml (32.9 mmol) of hydrazine hydrate and 40 ml of methanol is heated under reflux for 5 hours and then concentrated by evaporation in vacuo. Recrystallization of the residue from methanol yields the title compound; m.p. 245–246° C. (decomp.).

Step 41.3:
3-(4-Acetylamino-phenylamino)-4-cyano-5-(dimethylamino-methyleneamino)-pyrazole A suspension of 5.3 g (20.7 mmol) of 3-(4-acetylamino-phenylamino)-5-amino-4-cyano-pyrazole in 4.4 ml (24.9 mmol) of N,N-dimethylformamide diethyl acetal (97%) and 100 ml of toluene is heated under reflux for 4 hours. The reaction mixture is then cooled to room temperature and filtered and the filter residue is washed with toluene, yielding the title compound having a water content of 4.22%; m.p. 275–276° C. (decomp.).

EXAMPLE 42

4-(3-Chloro-phenylamino)-3-(4-hydroxy-phenylamino)-1H-pyrazolo[3,4-d]-pyrimidine Under a nitrogen atmosphere, a solution of 5 ml (51.9 mmol) of boron tribromide in 20 ml of methylene chloride is added dropwise over a period of 30 minutes to a suspension, cooled to 0° C., of 5 g (13.63 mmol) of 4-(3-chloro-phenylamino)-3-(4-methoxy-phenylamino)-1H-pyrazolo[3,4-d]pyrimidine in 100 ml of methylene chloride. The reaction mixture is stirred at 20° C. for 14 hours and then filtered and the filter residue is digested for ½ hour at RT in 85 ml of water. After filtering, the filter residue is partitioned between 50 ml of saturated sodium hydrogen carbonate solution, 50 ml of water and 135 ml of THF. The organic phase is separated off, the aqueous phase is extracted again with 35 ml of THF, the combined THF extracts are washed with brine and the organic phase is dried over sodium sulfate and concentration by evaporation is carried out in vacuo. The crystalline residue is digested in 65 ml of boiling ethyl acetate, cooled to RT and filtered, yielding the crude title compound. Recrystallization of a sample from ethyl acetate yields the pure title compound; m.p. >260° C.; TLC-$R_f$=0.54 (toluene/isopropanol/conc. ammonia [70:29:1]).

EXAMPLE 43

4-(3-Chloro-phenylamino)-3-(4-dimethylamino-phenylamino)-1H-pyrazolo-[3,4-d]pyrimidine A mixture of 5 g (16.8 mmol) of 4-cyano-5-(dimethylamino-methyleneamino)-3-(4-dimethylamino-phenylamino)-pyrazole, 3.3 g (20.1 mmol) of 3-chloro-aniline hydrochloride and 40 ml of DMF is heated for 8 hours, with stirring, at 130° C. The reaction mixture is then cooled to RT, water is added dropwise thereto, and the reaction mixture is then filtered and the filter residue is dissolved in approx. 20 ml of DMF. After precipitation with water, followed by recrystallization from DMF/water, the resulting crystals are suspended in 10 ml of water. 6 ml of 1N hydrochloric acid are added, the mixture is heated briefly to reflux and filtered and 3 ml of 2N sodium hydroxide solution are added to the filtrate. The crystalline precipitate is filtered off, washed with water and dried under a high vacuum at 120° C., yielding the title compound having a water content of 2.32%; m.p. 250–255° C. (decomp.).

The starting material is prepared as follows:

Step 43.1:
4-Cyano-5-(dimethylamino-methyleneamino)-3-(4-dimethylamino-phenylamino)-pyrazole A suspension of 10 g (41.3 mmol) of 5-amino-4-cyano-3-(4-dimethylamino-phenylamino)-pyrazole [for preparation see: Arch.Pharm.(Weinheim) 326, 245 (1993)] in 8.75 ml (49.5 mmol) of N,N-dimethylformamide diethyl acetal (97%) and 200 ml of toluene is heated under reflux for 1 hour. The reaction mixture is then cooled to approx. 30° C. and filtered and the filter residue is washed with toluene, yielding the title compound; m.p. 281–282° C. (decomp.).

EXAMPLE 44

4-(3-Chloro-phenylamino)-3-(4-methoxy-benzylamino)-1H-pyrazolo[3,4-d]-pyrimidine A mixture of 4.475 g (15 mmol) of 4-cyano-5-(dimethylamino-methyleneamino)-3-(4-methoxy-benzylamino)-pyrazole, 2.83 g (17.25 mmol) of 3-chloro-aniline hydrochloride and 80 ml of ethanol is heated under reflux for 16 hours. Cooling to approx. 5° C., filtering and washing the filter residue with diethyl ether yield the title compound; m.p. 222–223° C.

The starting material is prepared as follows:

Step 44.1:
2-Cyano-3-(4-methoxy-benzylamino)-3-methylmercapto-acrylonitrile

A mixture of 17.03 g (0.1 mol) of 3,3-bis-methylmercapto-2-cyano-acrylonitrile, 12.98 ml (0.1 mol) of 4-methoxy-benzylamine and 60 ml of ethanol is heated under reflux for 2 hours. Approx. 90 ml of hexane are then added dropwise to the hot solution which is then allowed to cool to RT. The title compound which has precipitated in the form of colorless crystals is filtered off, washed with diethyl ether and dried under a HV; m.p. 100–101° C.

Step 44.2:
5-Amino-4-cyano-3-(4-methoxy-benzylamino)-pyrazole

A mixture of 15 g (57.8 mmol) of 2-cyano-3-(4-methoxy-benzylamino)-3-methylmercapto-acrylonitrile, 3.03 ml (61.1 mmol) of hydrazine hydrate and 40 ml of methanol is stirred for 1 hour at RT, heated under reflux for 2 hours and then concentrated by evaporation in vacuo. Recrystallization of the residue from ethanol/hexane yields the title compound; m.p. 148–149° C.

Step 44.3:
4-Cyano-5-(dimethylamino-methyleneamino)-3-(4-methoxy-benzylamino)-pyrazole A mixture of 6.08 g (25 mmol) of 5-amino-4-cyano-3-(4-methoxy-benzylamino)-pyrazole, 5.14 ml (30 mmol) of N,N-dimethylformamide diethyl acetal and 90 ml of toluene is heated under reflux for 3 hours. The reaction mixture is then cooled to approx. 5° C. and filtered and the filter residue is washed with toluene, yielding the title compound; m.p. 147–148° C.

EXAMPLE 45

4-(3-Chloro-phenylamino)-3-(3-methoxy-benzylamino)-1H-pyrazolo[3,4-d]-pyrimidine (title compound I) and 5-(3-chloro-phenyl)-1,5-dihydro-4-imino-3-(3-methoxy-benzylamino)-4H-pyrazolo[3,4-d]pyrmidine hydrochloride (title compound II)

A mixture of 5.97 g (20 mmol) of 4-cyano-5-(dimethylamino-methyleneamino)-3-(3-methoxy-benzylamino)-pyrazole, 3.77 g (23 mmol) of 3-chloro-aniline hydrochloride and 100 ml of ethanol is heated under reflux for 36 hours. Cooling to approx. 10° C., filtering and washing the filter residue with ethanol yield title compound II; m.p. 251–253° C. (decomp.). The filtrate is concentrated by evaporation in vacuo, the oily residue is partitioned between ethyl acetate and water and the organic phase is washed with brine, dried over sodium sulfate and concentrated to a volume of approx. 25 ml using an RV, a crystalline precipitate being formed. Filtering and washing the filter residue with a small amount of ethyl acetate and diethyl ether yield title compound I (see Example 52); m.p. 194–195° C.

The starting material is prepared as follows:
Step 45.1:
2-Cyano-3-(3-methoxy-benzylamino)-3-methylmercapto-acrylonitrile A mixture of 17.03 g (0.1 mol) of 3,3-bis-methylmercapto-2-cyano-acrylonitrile, 12.78 ml (0.1 mol) of 3-methoxy-benzylamine and 60 ml of ethyl acetate is heated under reflux for 2 hours and then concentrated by evaporation in vacuo, yielding the oily title compound; TLC-$R_f$32 0.28 (toluene/isopropanol [9:1]).
Step 45.2:
5-Amino-4-cyano-3-(3-methoxy-benzylamino)-pyrazole A mixture of 25.57 g (98.6 mmol) of 2-cyano-3-(3-methoxy-benzylamino)-3-methylmercapto-acrylonitrile, 5.16 ml (104 mmol) of hydrazine hydrate and 140 ml of methanol is stirred at RT for 1 hour, heated under reflux for 2.5 hours and then concentrated by evaporation in vacuo. Recrystallization of the residue from ethanol/hexane yields the title compound; m.p. 151–153° C.
Step 45.3:
4-Cyano-5-(dimethylamino-methyleneamino)-3-(3-methoxy-benzylamino-pyrazole A mixture of 9.12 g (37.5 mmol) of 5-amino-4-cyano-3-(3-methoxy-benzylamino)-pyrazole, 7.71 ml (45 mmol) of N,N-dimethylformamide diethyl acetal and 130 ml of toluene is heated under reflux for 3 hours and then approx. 40 ml of hexane are added dropwise thereto. Cooling to 10° C. causes a crystalline precipitate to form. Filtering and washing the filter residue with diethyl ether yield the title compound; m.p. 136–137° C.

EXAMPLE 46

4-Benzylamino-3-(3-methyl-phenylamino)-1H-pyrazolo[3,4-d]pyrimidine

Under a nitrogen atmosphere, a mixture of 1 g (3.74 mmol) of 4-cyano-5-(dimethylamino-methyleneamino)-3-(3-methyl-phenylamino)-pyrazole and 10 ml of benzylamine is stirred for 4 hours at 120° C. and then concentrated by evaporation under a HV. The crystalline residue is digested in 10 ml of acetonitrile and filtered and the filter residue is recrystallized from 40 ml of acetonitrile, yielding the title compound; m.p. 200–201° C.

The starting material is prepared as follows:
Step 46.1:
4-Cyano-5-(dimethylamino-methyleneamino)-3-(3-methyl-phenylamino)-pyrazole A suspension of 10.71 g (50.22 mmol) of 5-amino-4-cyano-3-(3-methyl-phenylamino)-pyrazole [for preparation see: Arch. Pharm. (Weinheim) 326, 245 (1993)], 9.9 ml (57.8 mmol) of N,N-dimethylformamide diethyl acetal and 150 ml of toluene is heated under reflux for 4 hours. The reaction mixture is then cooled to RT and filtered and the filter residue is washed with toluene and diethyl ether, yielding the title compound; m.p. 260–261° C.

EXAMPLE 47

(S)-3-(3-Methyl-phenylamino)-4-(1-phenyl-ethylamino)-1H-pyrazolo[3,4-d]-pyrimidine hydrochloride Under a nitrogen atmosphere, a mixture of 1 g (3.74 mmol) of 4-cyano-5-(dimethylamino-methyleneamino)-3-(3-methyl-phenylamino)-pyrazole and 10 ml of (S)-1-phenyl-ethylamine is stirred at 120° C. for 24 hours and then concentrated by evaporation under a HV. The oily residue is purified by flash chromatography on silica gel having a particle size of 0.04–0.06 mm using ethyl acetate/hexane (7:3). The product-containing fractions are concentrated by evaporation and the resinous residue is dissolved in a mixture of 5 ml of ethanol and 0.8 ml of 4N hydrochloric acid. Concentration by evaporation again and recrystallization of the residue from ethanol/diethyl ether yield the title compound; m.p. 170–180° C. (decomp.); $[a]_D^{20}$=+253.8±1° (c=1.015%, methanol).

EXAMPLE 48

(R)-3-(3-Methyl-phenylamino)-4-(1-phenyl-ethylamino)-1H -pyrazolo[3,4-d]-pyrimidine hydrochloride Analogously to Example 47, the title compound [m.p. 170–180° C. (decomp.); $[a]_D^{20}$=−249.4±1° (c=0.987%, methanol)] is obtained from 1.5 g (5.61 mmol) of 4-cyano-5-(dimethylamino-methyleneamino)-3-(3-methyl-phenylamino)-pyrazole and 10 ml of (R)-1-phenyl-ethylamine.

EXAMPLE 49

4-Benzylamino-3-(3-chloro-phenylamino)-1H-pyrazolo[3,4-d]pyrimidine

Under a nitrogen atmosphere, a mixture of 1 g (3.46 mmol) of 3-(3-chloro-phenylamino)-4-cyano-5-(dimethylamino-methyleneamino)-pyrazole and 10 ml of benzylamine is stirred for 3 hours at 120° C. and then concentrated by evaporation under a HV. The crystalline residue is digested in 10 ml of acetonitrile, cooled to 0° C. and filtered and the filter residue is recrystallized from 35 ml of acetonitrile, yielding the title compound; m.p. 216–218° C.

The starting material is prepared as follows:
Step 49.1:
5-Amino-3-(3-chloro-phenylamino)-4-cyano-pyrazole A mixture of 15 g (60.1 mmol) of 3-(3-chloro-phenylamino)-2-cyano-3-methylmercapto-acrylonitrile [for preparation see: EP 0 010 396 A1], 3.13 ml (63.2 mmol) of hydrazine hydrate and 100 ml of methanol is heated under reflux for 3 hours and then concentrated by evaporation in vacuo. Recrystallization of the residue from ethyl acetate/hexane yields the title compound; m.p. 195–200° C.
Step 49.2:
3-(3-Chloro-phenylamino)-4-cyano-5-(dimethylamino-methyleneamino)-pyrazole Analogously to Step 44.3, the title compound [m.p. >260° C.; TLC-$R_f$=0.87 (methylene chloride/methanol [9:1])] is obtained from 11.7 g (50.07 mmol) of 5-amino-3-(3-chloro-phenylamino)-4-cyano-pyrazole, 9.43 ml (55.07 mmol) of N,N-dimethylformamide diethyl acetal and 140 ml of toluene after heating under reflux for 3.5 hours.

EXAMPLE 50
4-(3-Chloro-phenylamino)-3-(3-methoxy-phenylamino)-1H-pyrazolo[3,4-d]-pyrimidine A mixture of 1.38 g (4.85 mmol) of 4-cyano-5-(dimethylamino-methyleneamino)-3-(3-methoxy-phenylamino)-pyrazole, 0.915 g (5.58 mmol) of 3-chloro-aniline hydrochloride and 20 ml of methanol is heated under reflux for 16 hours. Concentration of the reaction mixture by evaporation in vacuo and recrystallization of the residue from methanol/water yield the title compound; m.p. 202–203° C.

The starting material is prepared as follows:
Step 50.1:
5-Amino-4-cyano-3-(3-methoxy-phenylamino)-pyrazole Analogously to Example 49.1, the title compound [m.p. 177–180° C.] is obtained from 10 g (40.77 mmol) of 2-cyano-3-(3-methoxy-phenylamino)-3-methylmercapto-acrylonitrile [for preparation see: Bioorg. Med. Chem. Lett. 4, 615 (1994)], 2.12 ml (42.8 mmol) of hydrazine hydrate and 70 ml of methanol after heating under reflux for 3.5 hours.
Step 50.2:
4-Cyano-5-(dimethylamino-methyleneamino)-3-(3-methoxy-phenylamino)-pyrazole Analogously to Example 44.3, the title compound [m.p. 227–231° C.] is obtained from 1.25 g (5.45 mmol) of 5-amino-4-cyano-3-(3-methoxy-phenylamino)-pyrazole, 1.23 ml (7.18 mmol) of N,N-dimethylformamide diethyl acetal and 25 ml of toluene after heating under reflux for 4.5 hours.

EXAMPLE 51
4-(3-Chloro-phenylamino)-3-(3-methoxy-phenylamino)-1H-pyrazolo[3,4-d]-pyrimidine A mixture of 0.9 g (2.45 mmol) of 5-(3-chloro-phenyl)-1,5-dihydro-4-imino-3-(3-methoxy-phenylamino)-4H-pyrazolo[3,4-d]pyrimidine, 18 ml of dioxane and 18 ml of water is heated under reflux for 10 hours. Cooling to 0° C., filtering and recrystallization from methanol/water and from methanol yield the title compound; m.p. 203–204° C.

The starting material is prepared as follows:
Step 51.1:
4-Cyano-5-(ethoxy-methyleneamino)-3-(3-methoxy-phenylamino)-pyrazole With stirring, a mixture of 4 g (17.45 mmol) of 5-amino-4-cyano-3-(3-methoxy-phenylamino)-pyrazole (Step 50.1) and 50 ml of orthoformic acid triethyl ester is heated at 120° C. for 1.5 hours, care being taken to ensure that the ethanol formed in the course of the reaction is distilled off from the reaction mixture. The reaction mixture is cooled to 30° C., approx. 100 ml of diethyl ether are added and the reaction mixture is cooled further to 0° C. and filtered. Washing with diethyl ether yields the title compound; m.p. 181–183° C.
Step 51.2:
5-(3-Chloro-phenyl)-1,5-dihydro-4-imino-3-(3-methoxy-phenylamino)-4H-pyrazolo[3,4-d]pyrimidine A mixture of 3.85 g (13.49 mmol) of 4-cyano-5-(ethoxy-methyleneamino)-3-(3-methoxy-phenylamino)-pyrazole, 2.84 ml (27.02 mmol) of 3-chloro-aniline and 75 ml of ethanol is heated under reflux for 2 hours. The reaction mixture is then cooled to RT and filtered. Washing the crystals with ethanol and diethyl ether yields the title compound; m.p. 190–192° C.

EXAMPLE 52
4-(3-Chloro-phenylamino)-3-(3-methoxy-benzylamino)-1H-pyrazolo[3,4-d]-pyrimidine A mixture of 0.417 g (1 mmol) of 5-(3-chloro-phenyl)-1,5-dihydro-4-imino-3-(3-methoxy-benzylamino)-4H-pyrazolo[3,4-d]pyrimidine hydrochloride (Example 45, title compound II), 20 ml of dioxane, 19 ml of water and 1 ml of 1N sodium hydroxide solution is heated under reflux for 10 hours. Cooling to approx. 5° C., filtering, washing the filter residue with water and drying under a HV at 120° C. yield the title compound (see Example 45); m.p. 192–193° C.

EXAMPLE 53
3-(3-Hydroxy-phenyl)-4-(3-chloro-phenylamino)-1H-pyrazolo[3,4-d]pyrimidine With the exclusion of air and moisture, a mixture of 44.2 mg (0.1 mmol) of 1-benzyl-4-(3-chloro-phenylamino)-3-(3-methoxy-phenyl)-pyrazolo[3,4-d]pyrimidine, 80 mg (0.6 mmol) of anhydrous aluminum chloride and 2 ml of toluene is heated under reflux for 2 hours. The reaction mixture is then poured into ice-water and extracted with ethyl acetate. The organic phase is washed with a saturated solution of sodium hydrogen carbonate in water and with brine, dried over sodium sulfate and concentrated by evaporation in vacuo. Purification of the residue by flash chromatography on silica gel (230–400 mesh) using methylene chloride and methylene chloride/methanol mixtures (19:1 and 17:3, respectively) yields the title compound; m.p. >220° C.; FAB-MS: $(M+H)^+$=338.

The starting material is prepared as follows:
Step 53.1:
2-Cyano-3-(3-methoxy-phenyl)-3-methylmercapto-acrylonitrile A mixture of 4.88 g (24.61 mmol) of 3-methoxy-dithiobenzoic acid methyl ester [for preparation see: Chem. Ber. 120,1757 (1987)], 4.26 g (29.56 mmol) of tetracyano-ethylene oxide (Fluka) and 35 ml of toluene is stirred for 1 hour at −5° C. and for 21 hours at 20° C. Then 2 ml of triethylamine are added to the reaction mixture, which is then concentrated while passing a stream of nitrogen through the reaction mixture for approx. 15 hours. The oily residue is purified by flash chromatography on silica gel (230–400 mesh) using hexane and hexane/-ethyl acetate mixtures having an increasing content of ethyl acetate (5%, 7.5%, 10%, 12.5% and 20% ethyl acetate). The product-containing fractions are concentrated by evaporation in vacuo, yielding the title compound in the form of an oil; TLC-$R_f$=0.48 (toluene/acetone [9:1]); FAB-MS: $(M+H)^+$= 231 ($C_{12}H_{10}N_2OS$).
Step 53.2:
5-Amino-1-benzyl-4-cyano-3-(3-methoxy-phenyl)-pyrazole At 5° C., 11.94 ml of a 5.4N solution of sodium methanolate in methanol (64.47 mmol) is added to a suspension of 6 g (30.62 mmol) of benzylhydrazine dihydrochloride in 15 ml of ethanol and the reaction mixture is stirred for approx. 15 minutes at 5–10° C. and then introduced into a suspension of 2.95 g (12.81 mmol) of 2-cyano-3-(3-methoxy-phenyl)-3-methyl-mercapto-acrylonitrile in 95 ml of ethanol. The reaction mixture is heated under reflux for 1 hour, then cooled to RT and filtered. The filter residue is washed with ethanol and the filtrate is concentrated by evaporation in vacuo. The oily residue is purified by flash chromatography on silica gel (230–400 mesh) using a toluene/acetone mixture (19:1). The combined product-containing fractions are concentrated by evaporation and the residue is digested in diisopropyl ether. Filtration yields the title compound; m.p. 147–149° C.; FAB-MS: $(M+H)^+$=305.

Step 53.3:
1-Benzyl-4-hydroxy-3-(3-methoxy-phenyl)-pyrazolo[3,4-d]pyrimidine

A mixture of 2.55 g (8.38 mmol) of 5-amino-1-benzyl-4-cyano-3-(3-methoxy-phenyl)-pyrazole and 20 ml of 85% aqueous formic acid is heated under reflux for 21 hours and then cooled to room temperature and, with stirring, a small amount of water is added thereto. Filtering and washing the filter residue with water yield the title compound; m.p. 183–185° C.; FAB-MS: $(M+H)^+=333$.

Step 53.4:
1-Benzyl-4-chloro-3-(3-methoxy-phenyl)-pyrazolo[3,4-d]pyrimidine

A mixture of 2.48 g (7.46 mmol) of 1-benzyl-4-hydroxy-3-(3-methoxy-phenyl)-pyrazolo[3,4-d]pyrimidine and 30 ml of phosphorus oxychloride is heated under reflux for 10 hours and then, with stirring, poured slowly into ice-water. The reaction mixture is stirred for a further 2 hours at 0–10° C. and filtered and the filter residue is washed with water. The crude product is dissolved in methylene chloride and the organic phase is washed with brine, dried over sodium sulfate and concentrated by evaporation in vacuo. Purification of the residue by flash chromatography on silica gel (230–400 mesh) using methylene chloride and methylene chloride/methanol mixtures (99:1 and 49:1) yields the title compound; m.p. 99–101° C.; FAB-MS: $(M+H)^+=351$.

Step 53.5:
1-Benzyl-4-(3-chloro-phenylamino)-3-(3-methoxy-phenyl-pyrazolo[3,4-d]-pyrimidine A mixture of 70 mg (0.2 mmol) of 1-benzyl-4-chloro-3-(3-methoxy-phenyl)-pyrazolo[3,4-d]-pyrimidine, 115.6 μl (1.1 mmol) of 3-chloro-aniline and 7 ml of 1-butanol is heated under reflux for 20 hours and then concentrated by evaporation in vacuo. The residue is digested in hexane and filtered. Repeated digestion of the filter residue in diisopropyl ether and in ethanol yields the title compound; m.p. 118–119° C.

EXAMPLE 54
4-(3-Chloro-phenylamino)-3-(4-hydroxy-phenyl)-1H-pyrazolo[3,4-d]pyrimidine With the exclusion of air and moisture, a mixture of 0.442 g (1.2 mmol) of 4-(3-chloro-phenylamino)-3-(4-methoxy-phenyl)-1H-pyrazolo[3,4-d]pyrimidine [see Example 34], 1.16 g (8.7 mmol) of anhydrous aluminum chloride and 20 ml of benzene is heated under reflux for 45 minutes. The reaction mixture is then poured into ice-water, filtered and washed with water and the filter residue is partitioned between a 5% solution of sodium hydrogen carbonate in water and ethyl acetate. The organic phase is washed with brine, dried over sodium sulfate and concentrated in vacuo. A small amount of hexane is added and the desired product precipitates. Washing with hexane and purification of the crude product by flash chromatography on silica gel (230–400 mesh) using an ethyl acetate/hexane mixture (7:3) yield the title compound; m.p. >220° C.; MS: $(M)^+=337$.

EXAMPLE 55
(R)-3-(3-Chloro-phenylamino)-4-(1-phenyl-ethylamino)-1H-pyrazolo[3,4-d]-pyrimidine hydrochloride Under a nitrogen atmosphere, a mixture of 1.5 g (5.19 mmol) of 3-(3-chloro-phenylamino)-4-cyano-5-(dimethylamino-methyleneamino)-pyrazole (Step 49.2) and 10 ml of (R)-1-phenylethylamine is stirred at 120° C. for 40 hours and then concentrated by evaporation under a HV. The oily residue is purified by flash chromatography on silica gel having a particle size of 0.04–0.06 mm using ethyl acetate/hexane (7:3). The product-containing fractions are concentrated by evaporation and the resinous residue is dissolved in a mixture of 5 ml of ethanol and 1.4 ml of 4N hydrochloric acid. Concentration by evaporation again and recrystallization of the residue from ethanol/diethyl ether and from ethanol yield the title compound; m.p. 150–152° C.; EI-MS: $(M)^+=364$; $[a]_D^{20}=-233.7\pm2.1°$ (c=0.486% methanol).

EXAMPLE 56
(S)-3-(3-Chloro-phenylamino)-4-(1-phenyl-ethylamino)-1H-pyrazolo[3,4-d]-pyrimidine hydrochloride 0.4 g (1.1 mmol) of (S)-3-(3-chloro-phenylamino)-1,5-dihydro-4-imino-5-(1-phenyl-ethyl)-4H-pyrazolo[3,4-d]pyrimidine in the molten state is stirred for 15 minutes at 220° C. The crude product obtained after cooling to RT is purified by flash chromatography on silica gel having a particle size of 0.04–0.06 mm using ethyl acetate/hexane (7:3). The product-containing fractions are concentrated by evaporation and the resinous residue is dissolved in ethanol. The addition of 0.6 ml of 4N hydrochloric acid, concentration by evaporation in vacuo and recrystallization of the residue from ethanol yield the title compound; m.p. 153–155° C.; EI-MS: $(M)^+=364$; $[a]_D^{20}=+232.7\pm2.2°$ (c=0.465%, methanol).

The starting material is prepared as follows:
Step 56.1:
3-(3-Chloro-phenylamino)-4-cyano-5-(ethoxy-methyleneamino)-pyrazole Analogously to Step 51.1, the title compound [m.p. 197–199° C.] is obtained from 4.5 g (19.26 mmol) of 5-amino-3-(3-chloro-phenylamino)-4-cyano-pyrazole (Step 49.1) and 50 ml of orthoformic acid triethyl ester after stirring for 2 hours at 120° C.

Step 56.2:
(S)-1,5-Dihydro-3-(3-chloro-phenylamino)-4-imino-5-(1-phenyl-ethyl)-4H-pyrazolo[3,4-d]pyrimidine Analogously to Step 51.2, the title compound [m.p. 214–215° C.; $[a]_D^{20}=-279.6\pm1°$ (c=0.98%, methanol)] is obtained from 1.2 g (4.14 mmol) of 3-(3-chloro-phenylamino)-4-cyano-5-(ethoxy-methyleneamino)-pyrazole, 0.632 ml (4.97 mmol) of (S)-1-phenyl-ethylamine and 12 ml of ethanol after heating under reflux for 2 hours.

EXAMPLE 57
3-(4-Acetylamino-benzylamino)-4-(3-chloro-phenylamino)-1H-pyrazolo[3,4-d]-pyrimidine A mixture of 0.34 g (1.04 mmol) of 3-(4-acetylamino-benzylamino)-4-cyano-5-(dimethylamino-methyleneamino)-pyrazole, 0.189 g (1.15 mmol) of 3-chloro-aniline hydrochloride and 4 ml of methanol is heated under reflux for 20 hours. Cooling to approx. 20° C., filtering and washing the filter residue with diethyl ether yields the title compound; m.p. >260° C.; TLC-$R_f$=0.34 (toluene/isopropanol/conc. ammonia [70:29:1]).

The starting material is prepared as follows:
Step 57.1:
3-(4-Amino-benzylamino)-2-cyano-3-methylmercapto-acrylonitrile A mixture of 17.03 g (0.1 mol) of 3,3-bis-methylmercapto-2-cyano-acrylonitrile, 11.34 ml (0.1 mol) of 4-amino-benzylamine (Aldrich) and 60 ml of ethanol is stirred at 50° C. for 2 hours and then concentrated by evaporation in vacuo. Purification of the residue by flash chromatography on silica gel having a particle size of 0.04–0.06 mm using toluene/isopropanol mixtures (49:1, 97:3, 24:1 and 9:1) yields the title compound; m.p. 100–102° C.

Step 57.2:
5-Amino-3-(4-amino-benzylamino)-4-cyano-pyrazole

A mixture of 15.71 g (64.3 mmol) of 3-(4-amino-benzylamino)-2-cyano-3-methylmercapto-acrylonitrile, 3.35 ml (67.5 mmol) of hydrazine hydrate and 90 ml of methanol is stirred for 1 hour at 20° C., heated under reflux for 4 hours and then concentrated by evaporation in vacuo. Digestion of the crystalline residue in 70 ml of diisopropyl ether, filtering and digestion again in 100 ml of isopropanol yield the title compound; m.p. 168–170° C.

Step 57.3:
3-(4-Acetylamino-benzylamino)-5-amino-4-cyano-pyrazole

With stirring, a solution of 1.087 ml (11.5 mmol) of acetic anhydride in 20 ml of THF is added dropwise over a period of 15 minutes, to a suspension, cooled to 0° C., of 2.5 g (10.95 mmol) of 5-amino-3-(4-amino-benzylamino)-4-cyano-pyrazole in 50 ml of THF. The reaction mixture is stirred for a further 2 hours at RT, there initially being formed a solution from which crystalline product gradually precipitates. The reaction mixture is filtered and the filter residue is washed with THF and diethyl ether. Drying under a HV (8 hours, 110° C.) yields the title compound containing 21.06% THF; m.p. 124–126° C. (decomp.); FAB-MS: $(M+H)^+ 271$ ($C_{13}H_{14}N_6O$).

Step 57.4:
3-(4-Acetylamino-benzylamino)-4-cyano-5-(dimethylamino-methyleneamino)-pyrazole A mixture of 0.48 g (1.4 mmol) of 3-(4-acetylamino-benzylamino)-5-amino-4-cyano-pyrazole containing 21.06% THF, 0.245 ml (1.43 mmol) of N,N-dimethylformamide diethyl acetal and 4 ml of toluene is heated under reflux for 4.5 hours. The reaction mixture is then cooled to approx. 0° C. and filtered and the filter residue is washed with toluene, yielding the title compound; m.p. 206–211° C.

EXAMPLE 58
3-(4-Amino-phenylamino)-4-(3-chloro-phenylamino)-1H-pyrazolo[3,4-d]-pyrimidine hydrochloride A mixture of 0.25 g (0.553 mmol) of 3-[4-(N-BOC-amino)-phenylamino]-4-(3-chloro-phenylamino)-1H-pyrazolo[3,4-d]pyrimidine (see Example 65) and 10 ml of a 3N solution of hydrochloric acid in methanol is stirred at RT for 20 hours. Then 10 ml of diethyl ether are added, the reaction mixture is filtered and the filter residue is digested in hot methanol. After cooling, filtering and washing the filter residue with diethyl ether, the crystals are dried for 15 hours under a high vacuum at 100° C. and then left to stand under ambient conditions for 24 hours, yielding the title compound containing 10.97% hydrogen chloride and 4.34% water; m.p. 211–213° C.; EI-MS: $(M)^+=351$.

EXAMPLE 59
4-(3-Chloro-phenylamino)-3-(3-hydroxy-phenylamino)-1H-pyrazolo[3,4-d]-pyrimidine With the exclusion of air and moisture, a mixture of 0.5 g (1.36 mmol) of 4-(3-chloro-phenylamino)-3-(3-methoxy-phenylamino)-1H-pyrazolo[3,4-d]pyrimidine (Example 50), 0.873 g (6.55 mmol) of anhydrous aluminum chloride and 15 ml of benzene is heated at 80° C. for 9 hours. The benzene phase is then decanted off, the resinous residue is partitioned between ethyl acetate and water and the organic phase is washed with water and with a saturated solution of sodium hydrogen carbonate in water, dried over sodium sulfate and concentrated by evaporation in vacuo. The residue is purified by flash chromatography on silica gel having a particle size of 0.04–0.06 mm using methylene chloride/methanol mixtures (50:1 and 20:1). The product-containing fractions are combined and concentrated to a volume of approx. 10 ml, the desired product crystallising out. Filtering and washing the filter residue with diethyl ether yield the title compound; m.p. 265–266° C.; EI-MS: $(M)^+=352$.

EXAMPLE 60
4-Benzylamino-3-(3-chloro-phenylamino)-1H-pyrazolo[3,4-d]pyrimidine A mixture of 1 g (4.28 mmol) of 5-amino-3-(3-chloro-phenylamino)-4-cyano-pyrazole (Step 49.1), 3.67 g (34.25 mmol) of benzylamine, 0.245 ml (4.28 mmol) of glacial acetic acid and 0.73 ml (19.35 mmol) of formic acid is heated at 200° C. for 20 hours. The reaction mixture is cooled to RT, 30 ml of ice-water and 5 ml of ethanol are added and stirring is carried out for a further 20 minutes. The reaction mixture is then filtered and the filter residue is washed with water. Recrystallization from isopropyl alcohol yields the title compound; m.p. 215–218° C.

EXAMPLE 61
4-Benzylamino-3-(3-chloro-phenylamino)-1H-pyrazolo[3,4-d]pyrimidine A mixture of 1 g (4.28 mmol) of 5-amino-3-(3-chloro-phenylamino)-4-cyano-pyrazole (Step 49.1) and 1.75 g (12.95 mmol) of N-benzylformamide (Aldrich) is heated at 200° C. for 20 hours. The reaction mixture is purified by flash chromatography on silica gel having a particle size of 0.04–0.06 mm using ethyl acetate. Concentration of the product-containing fractions by evaporation and recrystallization of the residue from ethyl acetate/hexane yield the title compound; m.p. 215–218° C.; FAB-MS: $(M+H)^+=351$.

EXAMPLE 62
3-(4-Amino-benzylamino)-4-(3-chloro-phenylamino)-1H-pyrazolo[3,4-d]-pyrimidine A mixture of 0.11 g (0.27 mmol) of 3-(4-acetylamino-benzylamino)-4-(3-chlorophenylamino)-1H-pyrazolo[3,4-d]pyrimidine (Example 57), 3 ml of water and 1.5 ml of 30% sodium hydroxide solution is heated at 100° C. for 4 hours. After cooling to RT, the reaction mixture is extracted with ethyl acetate and the extract is washed with brine, dried over sodium sulfate and concentrated by evaporation in vacuo. The residue is purified by flash chromatography on silica gel having a particle size of 0.04–0.06 mm using methylene chloride/methanol mixtures (50:1 and 20:1). The product-containing fractions are concentrated by evaporation and the residue is recrystallized from ethyl acetate/hexane, yielding the title compound; m.p. 170–171° C.; EI-MS: $(M)^+=365$.

EXAMPLE 63
4-(3-Chloro-phenylamino)-3-(4-ethoxy-phenylamino)-1H-pyrazolo[3,4-d]-pyrimidine A mixture of 5.8 g (19.44 mmol) of 4-cyano-5-(dimethylamino-methyleneamino)-3-(4-ethoxy-phenylamino)-pyrazole, 3.51 g (21.4 mmol) of 3-chloro-aniline hydrochloride and 40 ml of methanol is heated under reflux for 15 hours. Cooling to 10° C., filtering and washing the filter residue with methanol and diethyl ether yield the title compound; m.p. 232–233° C.; EI-MS: $(M)^+=380$.

The starting material is prepared as follows:
Step 63.1:
2-Cyano-3-(4-ethoxy-phenylamino)-3-methylmercapto-acrylonitrile A mixture of 17.03 g (0.1 mol) of 3,3-bis-methylmercapto-2-cyano-acrylonitrile, 12.94 ml (0.1 mol) of 4-ethoxy-aniline and 60 ml of ethanol is heated under reflux for 2 hours. Then, with stirring, 120 ml of diethyl ether are added dropwise to the reaction mixture, which is at approx. 30° C. The reaction mixture is then cooled to 0° C. The title compound precipitates in the form of colorless crystals and is filtered off, washed with diethyl ether and dried under a HV; m.p. 141–142° C.

Step 63.2:
5-Amino-4-cyano-3-(4-ethoxy-phenylamino)-pyrazole

A mixture of 21.5 g (82.9 mmol) of 2-cyano-3-(4-ethoxy-phenylamino)-3-methylmercapto-acrylonitrile, 4.31 ml (87 mmol) of hydrazine hydrate and 110 ml of methanol is heated under reflux for 7 hours and then concentrated by evaporation in vacuo. Recrystallization of the residue from ethyl acetate/hexane yields the title compound; m.p. 166–167° C.

Step 63.3:
4-Cyano-5-(dimethylamino-methyleneamino)-3-(4-ethoxy-phenylamino)-pyrazole A suspension of 4.86 g (19.98 mmol) of 5-amino-4-cyano-3-(4-ethoxy-phenylamino)-pyrazole in 3.94 ml (23 mmol) of N,N-dimethylformamide diethyl acetal and 60 ml of toluene is heated under reflux for 2 hours. The reaction mixture is then cooled to 20° C. and filtered and the filter residue is washed with toluene, yielding the title compound; m.p. 246–247° C. (decomp.).

EXAMPLE 64

The following compounds are obtained analogously to the processes described in this text, e.g. in Examples 40–63:

a) 4-(3-chloro-phenylamino)-3-(3,4-dimethoxy-phenylamino)-1H-pyrazolo[3,4-d]pyrimidine; m.p. 168–170° C.

b) 4-(3-chloro-phenylamino)-3-(3,5-dimethoxy-phenylamino)-1H-pyrazolo[3,4-d]pyrimidine; m.p. 218–220cC c) 4-(3-chloro-phenylamino)-3-(3-formylamino-4-methoxy-phenylamino)-1H-pyrazolo[3,4-d]-pyrimidine d) 3-(3-acetylamino-4-methoxy-phenylamino)-4-(3-chloro-phenylamino)-1H-pyrazolo[3,4-d]-pyrimidine e) 3-(4-acetylamino-3-methoxy-phenylamino)-4-(3-chloro-phenylamino)-1H-pyrazolo[3,4-d]-pyrimidine f) 4-(3-chloro-phenylamino)-3-(4-formylamino-phenylamino)-1H-pyrazolo[3,4-d]pyrimidine g) 4-(3-chloro-phenylamino)-3-(4-formylamino-benzylamino)-1H-pyrazolo[3,4-d]pyrimidine h) 4-(3-chloro-phenylamino)-3-(4-propionylamino-benzylamino)-1H-pyrazolo[3,4-d]pyrimidine i) 3-(4-aminomethyl-phenylamino)-4-(3-chloro-phenylamino)-1H-pyrazolo[3,4-d]pyrimidine hydrate; m.p. 207–209° C.

k) 3-(3-aminomethyl-phenylainino)-4-(3-chloro-phenylamino)-1H-pyrazolo[3,4-d]pyrimidine l) 3-[4-(N-BOC-aminomethyl)-phenylamino]-4-(3-chloro-phenylamino)-1H-pyrazolo[3,4-d]-pyrimidine-hydrate [precursor of i)]; m.p. 196° C.

m) 3-[3-(N-BOC-aminomethyl)-phenylamino]-4-(3-chloro-phenylamino)-1H-pyrazolo[3,4-d]-pyrimidine [precursor of k)].

n) 4-(3-chloro-phenylamino)-3-(4-methylsulphonylaminomethyl-phenylamino)-1H-pyrazolo[3,4-d]pyrimidine n) 4-(3-chloro-phenylamino)-3-(3-methylsulphonylaminomethyl-phenylamino)-1H-pyrazolo[3,4-d]pyrimidine o) 4-(3-chloro-phenylamino)-3-(4-formylaminomethyl-phenylamino)-1H-pyrazolo[3,4-d]pyrimidine p) 4-(3-chloro-phenylamino)-3-(3-formylaminomethyl-phenylamino)-1H-pyrazolo[3,4-d]pyrimidine q) 3-(4-acetylaminomethyl-phenylamino)-4-(3-chloro-phenylamino)-1H-pyrazolo[3,4-d]pyrimidine r) 3-(3-acetylaminomethyl-phenylamino)-4-(3-chloro-phenylamino)-1H-pyrazolo[3,4-d]pyrimidine s) 4-(3-chloro-phenylamino)-3-(4-methylsulphonylamino-phenylamino)-1H-pyrazolo[3,4-d]pyrimidine; m.p. >260° C., APCI-MS: (M+H)$^+$= 430 t) 4-(3-chloro-phenylamino)-3-(3-methylsulphonylamino-phenylamino)-1H-pyrazolo[3,4-d]pyrimidine EXAMPLE 65
3-14-(N-BOC-Amino)-phenylaminol-4-(3-chloro-phenylamino)-1H-pyrazolo-[3,4-d]pyrimidine With stirring, a mixture of 2 g (4.43 mmol) of 1,5-dihydro-3-[4-(N-BOC-amino)-phenylamino]-4-imino-5-(3-chloro-phenyl)-4H-pyrazolo[3,4-d]pyrimidine, 40 ml of dioxane and 40 ml of water is heated at 120° C. for 22 hours. Cooling to 20° C., filtering and washing the filter residue with dioxane yield the title compound; m.p. 256–258° C.

The starting material is prepared as follows:
Step 65.1:
3-[4-(N-BOC-Amino)-phenylamino]-2-cyano-3-methylmercapto-acrylonitrile A mixture of 13.89 g (81.58 mmol) of 3,3-bis-methylmercapto-2-cyano-acrylonitrile, 17 g (81.63 mmol) of N-BOC-1,4-phenylenediamine (Fluka) and 200 ml of methanol is heated under reflux for 5 hours. Cooling to room temperature, filtering and washing the filter residue with methanol yield the title compound; m.p. 190° C. Concentration of the filtrate by evaporation and recrystallization of the residue from 50 ml of methanol yield a further batch of the title compound; m.p. 190–191° C.

Step 65.2:
5-Amino-3-[4-(N-BOC-amino)-phenylamino]-4-cyano-pyrazole

Analogously to Example 49.1, the title compound [m.p. 166–168° C.] is obtained from 23.1 g (69.91 mmol) of 3-[4-(N-BOC-amino)-phenylamino]-2-cyano-3-methylmercapto-acrylonitrile, 4.15 ml (83.75 mmol) of hydrazine hydrate and 200 ml of methanol after heating under reflux for 5 hours.

Step 65.3:
3-[4-(N-BOC-Amino)-phenylamino]-4-cyano-5-(ethoxy-methyleneamino)-pyrazole With stirring, a mixture of 13.8 g (43.9 mmol) of 5-amino-3-[4-(N-BOC-amino)-phenylamino]-4-cyano-pyrazole and 138 ml of orthoformic acid triethyl ester is heated at 120° C. for 3 hours, care being taken to ensure that the ethanol formed in the course of the reaction is distilled off from the reaction mixture. Cooling to RT, filtering and washing the filter residue with ethanol yield the title compound; m.p. 180–182° C.

Step 65.4:
1,5-Dihydro-3-[4-(N-BOC-amino)-phenylamino]-4-imino-5-(3-chloro-phenyl)-4H-pyrazolo[3,4-d]pyrimidine A mixture of 7 g (18.9 mmol) of 3-[4-(N-BOC-amino)-phenylamino]-4-cyano-5-(ethoxy-methyleneamino)-pyrazole, 3.97 ml (37.78 mmol) of 3-chloro-aniline and 150 ml of ethanol is heated under reflux for 9 hours and stirred at room temperature for a further 15 hours. Filtering and washing the filter residue with cold ethanol yield the title compound; m.p. 229–234° C. (decomp.); FAB-MS: (M+H)$^+$=452.

EXAMPLE 66

Dry-Filled Capsules 5000 capsules, each comprising as active ingredient 0.25 g of one of the compounds of formula I mentioned in Examples 1 to 65, are prepared as follows:

| Composition | |
|---|---|
| active ingredient | 1250 g |
| talcum | 180 g |
| wheat starch | 120 g |
| magnesium stearate | 80 g |
| lactose | 20 g |

Preparation process: The mentioned substances are pulverized and forced through a sieve of 0.6 mm mesh size. 0.33 g portions of the mixture are introduced into gelatin capsules using a capsule-filling machine.

EXAMPLE 67

Soft Capsules 5000 soft gelatin capsules, each comprising as active ingredient 0.05 g of one of the compounds of formula I mentioned in Examples 1 to 65, are prepared as follows:

| Composition | |
|---|---|
| active ingredient | 250 g |
| Lauroglycol | 2 liters |

Preparation process: The pulverized active ingredient is suspended in Lauroglycol (propylene glycol laurate, Gattefossé S. A., Saint Priest, France) and ground in a wet pulveriser to a particle size of approx. from 1 to 3 mm. 0.419 g portions of the mixture are then introduced into soft gelatin capsules using a capsule-filling machine.

EXAMPLE 68

Soft Capsules 5000 soft gelatin capsules, each comprising as active ingredient 0.05 g of one of the compounds of formula I mentioned in Examples 1 to 65, are prepared as follows:

| Composition | |
|---|---|
| active ingredient | 250 g |
| PEG 400 | 1 liter |
| Tween 80 | 1 liter |

Preparation process: The pulverized active ingredient is suspended in PEG 400 (polyethylene glycol having an $M_r$ of from approx. 380 to approx. 420, Fluka, Switzerland) and Tween 80 (polyoxyethylene sorbitan monolaurate, Atlas Chem. Ind. Inc., USA, supplied by Fluka, Switzerland) and ground in a wet pulverized to a particle size of approx. from 1 to 3 mm. 0.43 g portions of the mixture are then introduced into soft gelatin capsules using a capsule-filling machine.

What is claimed is:

1. A 4-amino-1H-pyrazolo[3,4-d]pyrimidine derivative of formula I

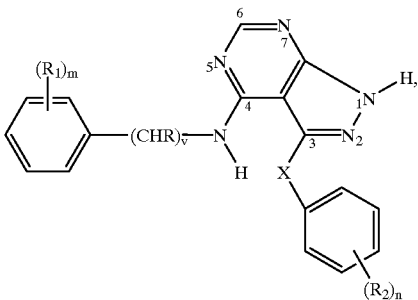

wherein m and n are each independently of the other an integer from 0 up to and including 3, v is 0 or 1, R is hydrogen or lower alkyl, $R_1$ is halogen, cyano, trifluoromethyl, hydroxy, lower alkoxy, lower alkanoyloxy, carboxy, lower alkoxycarbonyl, carbamoyl, N-lower alkylcarbamoyl, or lower alkyl that is unsubstituted or substituted by amino or by cyano, it being possible when several phenyl substituents $R_1$ are present for those substituents to be identical or different from one another, X is the group $NH(CH-R_7)_t$ wherein t is an integer from 0 up to and including 3 and $R_7$ is hydrogen or lower alkyl, or the group $(C[R_3]-R_4)_q$ wherein q is an integer from 0 up to and including 3 with the proviso that q and n are not simultaneously 0, $R_3$ is hydrogen or lower alkyl and $R_4$ is hydrogen or lower alkyl, and $R_2$ is halogen, nitro, cyano, trifluoromethyl, carboxy, lower alkoxycarbonyl, carbamoyl, N-lower alkylcarbamoyl, N,N-di-lower alkylcarbamoyl, azido, amino, lower alkylamino, di-lower alkylamino, di-lower alkylamino-lower alkyleneamino, benzylamino, benzoylamino, lower alkanoylamino, lower alkoxycarbonylamino, benzyloxycarbonylamino, thien-2-ylcarbonylamino, fur-2-ylcarbonylamino, pyrid-2-ylcarbonylamino, lower alkylsulfonylamino, benzenesulfonylamino, p-toluenesulfonylamino, hydroxy, lower alkanoyloxy, oxa-lower alkoxy, lower alkoxy that is unsubstituted or substituted by carboxy, lower alkoxycarbonyl, carbamoyl or by N-lower alkylcarbamoyl, or lower alkyl that is unsubstituted or substituted by amino, lower alkanoylamino, benzoylamino, lower alkoxycarbonylamino, lower alkylsulfonylamino, benzenesulfonylamino, p-toluenesulfonylamino, cyano, hydroxy, lower alkanoyloxy, lower alkoxycarbonyloxy or by lower alkoxy, it being possible when several phenyl substituents $R_2$ are present for those substituents to be identical or different from one another and for two vicinal radicals $R_2$ together also to form methylenedioxy, or a salt or a tautomer of such a compound.

2. A compound of formula I according to claim 1, wherein m is 0 or 1, n is an integer from 1 up to and including 3, v is 0 or 1, R is hydrogen or lower alkyl, $R_1$ is halogen or lower alkyl that is unsubstituted or substituted by amino or by cyano, X is the group NH(CH—$R_7$)$_t$, wherein t is 0 or 1 and $R_7$ is hydrogen or lower alkyl, or the group (C[$R_3$]—$R_4$)$_q$ wherein q is 0, and $R_2$ is halogen, nitro, carboxy, lower alkoxycarbonyl, carbamoyl, N-lower alkylcarbamoyl, N,N-di-lower alkylcarbamoyl, amino, lower alkylamino, di-lower alkylamino, di-lower alkylaminomethyleneamino, benzylamino, benzoylamino, lower alkanoylamino, lower alkoxycarbonylamino, benzyloxycarbonylamino, thien-2-ylcarbonylamino, fur-2-ylcarbonylamino, pyrid-2-ylcarbonylamino, lower alkylsulfonylamino, benzenesulfonylamino, p-toluenesulfonylamino, hydroxy, lower alkanoyloxy, lower alkoxy, or lower alkyl that is unsubstituted or substituted by amino, lower alkanoylamino, benzoylamino or by lower alkoxycarbonylamino, it being possible when several phenyl substituents $R_2$ are present for those substituents to be identical or different from one another and for two vicinal radicals $R_2$ together also to form methylenedioxy, or a salt of such a compound.

3. A compound of formula I according to claim 1, selected from 3-benzylamino-4-(3-chloro-phenylamino)-1H-pyrazolo[3,4-d]pyrimidine, 4-(3-chloro-phenylamino)-3-(4-methoxycarbonylbenzylamino)-1H-pyrazolo[3,4-d]pyrimidine, 3-(4-carboxy-benzylamino)-4-(3-chloro-phenylamino)-1H-pyrazolo[3,4-d]pyrimidine, 4-(3-chloro-phenylamino)-3-[3-(methylaminocarbonyl)-benzylamino]-1H-pyrazolo[3,4-d]-pyrimidine, 4-(3-chloro-phenylamino)-3-[4-(methylaminocarbonyl)-benzylamino]-1H-pyrazolo[3,4-d]-pyrimidine, 4-(3-chloro-phenylamino)-3-(3,5-dimethoxy-benzylamino)-1H-pyrazolo[3,4-d]pyrimidine, 4-(3-chloro-phenylamino)-3-[(3-methoxy-4-hydroxy-benzyl)-amino]-1H-pyrazolo[3,4-d]-pyrimidine, 4-(3-chloro-phenylamino)-3-(3-methoxycarbonyl-benzylamino)-1H-pyrazolo[3,4-d]pyrimidine, 4-(3-chloro-phenylamino)-3-(3,4,5-trimethoxy-benzylamino)-1H-pyrazolo[3,4-d]pyrimidine, 4-(3-chloro-phenylamino)-3-(3,4-dimethoxy-benzylamino)-1H-pyrazolo[3,4-d]pyrimidine, 4-(3-chloro-phenylamino)-3-(2,3,4-trimethoxy-benzylamino)-1H-pyrazolo[3,4-d]pyrimidine, 4-(3-chloro-phenylamino)-3-(3-hydroxy-4-methoxy-benzylamino)-1H-pyrazolo[3,4-d]-pyrimidine, 4-(3-chloro-phenylamino)-3-(4-hydroxy-3,5-dimethoxy-benzylamino)-1H-pyrazolo[3,4-d]-pyrimidine, 4-(3-chloro-phenylamino)-3-(3,4-methylenedioxy-benzylamino)-1H-pyrazolo[3,4-d]pyrimidine, 4-(3-chloro-phenylamino)-3-(2,3-methylenedioxy-benzylamino)-1H-pyrazolo[3,4-d]-pyrimidine, 3-(3-chloro-benzylamino)-4-(3-chloro-phenylamino)-1H-pyrazolo[3,4-d]pyrimidine, 3-(3-chloro-4-hydroxy-benzylamino)-4-(3-chloro-phenylamino)-1H-pyrazolo[3,4-d]pyrimidine, 3-(3-chloro-4-methoxy-benzylamino)-4-(3-chloro-phenylamino)-1H-pyrazolo[3,4-d]pyrimidine, 4-(3-chloro-phenylamino)-3-{[1-(3-chloro-phenyl)-ethyl]-amino}-1H-pyrazolo[3,4-d]pyrimidine, 4-(3-chloro-phenylamino)-3-[(1-phenyl-ethyl)-amino]-1H-pyrazolo[3,4-d]pyrimidine, 4-(3-chloro-phenylamino)-3-[3-(dimethylaminocarbonyl)-benzylamino]-1H-pyrazolo[3,4-d]-pyrimidine, 4-(3-chloro-phenylamino)-3-(4-methoxy-phenyl)-1H-pyrazolo[3,4-d]pyrimidine, 3-(4-amino-phenyl)-4-(3-chloro-phenylamino)-1H-pyrazolo[3,4-d]pyrimidine, 3-(4-tert-butoxycarbonylamino-phenyl)-4-(3-chloro-phenylamino)-1H-pyrazolo[3,4-d]-pyrimidine, 4-(3-chloro-phenylamino)-3-(3-nitro-phenyl)-1H-pyrazolo[3,4-d]pyrimidine, 3-(3-amino-phenyl)-4-(3-chloro-phenylamino)-1H-pyrazolo[3,4-d]pyrimidine, 4-(3-chloro-phenylamino)-3-(4-[3-methyl-butanoyl-amino]-phenyl)-1H-pyrazolo[3,4-d]-pyrimidine, 4-(3-chloro-phenylamino)-3-(3-[3-methyl-butanoyl-amino]-phenyl)-1H-pyrazolo[3,4-d]-pyrimidine, 4-(3-chloro-phenylamino)-3-(4-propanoylamino-phenyl)-1H-pyrazolo[3,4-d]pyrimidine, 4-(3-chloro-phenylamino)-3-(3-propanoylamino-phenyl)-1H-pyrazolo[3,4-d]pyrimidine, 4-(3-chloro-phenylamino)-3-(4-pivaloylamino-phenyl)-1H-pyrazolo[3,4-d]pyrimidine, 4-(3-chloro-phenylamino)-3-(3-pivaloylamino-phenyl)-1H-pyrazolo[3,4-d]pyrimidine, 3-(4-acetylamino-phenyl)-4-(3-chloro-phenylamino)-1H-pyrazolo[3,4-d]pyrimidine, 3-(3-acetylamino-phenyl)-4-(3-chloro-phenylamino)-1H-pyrazolo[3,4-d]pyrimidine, 4-(3-chloro-phenylamino)-3-(4-{[N,N-dimethylamino}-methyleneamino]-phenyl)-1H-pyrazolo[3,4-d]pyrimidine, 4-(3-chloro-phenylamino)-3-(3-{[N,N-dimethylamino}-methyleneamino]-phenyl)-1H-pyrazolo[3,4-d]pyrimidine, 4-(3-chloro-phenylamino)-3-(4-[thien-2-yl-carbonylamino]-phenyl)-1H-pyrazolo[3,4-d]-pyrimidine, 4-(3-chloro-phenylamino)-3-(3-[thien-2-yl-carbonylamino]-phenyl)-1H-pyrazolo[3,4-d]-pyrimidine, 4-(3-chloro-phenylamino)-3-(4-[fur-2-yl-carbonylamino]-phenyl)-1H-pyrazolo[3,4-d]-pyrimidine, 4-(3-chloro-phenylamino)-3-(3-[fur-2-yl-carbonylamino]-phenyl)-1H-pyrazolo[3,4-d]-pyrimidine, 4-(3-chloro-phenylamino)-3-(4-[pyrid-2-yl-carbonylamino]-phenyl)-1H-pyrazolo[3,4-d]-pyrimidine, 4-(3-chloro-phenylamino)-3-(3-[pyrid-2-yl-carbonylamino]-phenyl)-1H-pyrazolo[3,4-d]-pyrimidine, 4-(3-chloro-phenylamino)-3-(4-methylsulfonylamino-phenyl)-1H-pyrazolo[3,4-d]pyrimidine, 4-(3-chloro-phenylamino)-3-(3-methylsulfonylamino-phenyl)-1H-pyrazolo[3,4-d]pyrimidine, 4-(3-chloro-phenylamino)-3-(4-[4-methyl-benzenesulfonylamino]-phenyl)-1H-pyrazolo[3,4-d]-pyrimidine, 4-(3-chloro-phenylamino)-3-(3-[4-methyl-benzenesulfonylamino]-phenyl)-1H-pyrazolo[3,4-d]-pyrimidine, 3-(3-tert-butoxycarbonylamino-phenyl)-4-(3-chloro-phenylamino)-1H-pyrazolo[3,4-d]-pyrimidine,
3-(4-benzyloxycarbonylamino-phenyl)-4-(3-chloro-phenylamino)-1H-pyrazolo[3,4-d]-pyrimidine,
3-(3-benzyloxycarbonylamino-phenyl)-4-(3-chloro-phenylamino)-1H-pyrazolo[3,4-d]-pyrimidine,
3-(4-acetylamino-phenylamino)-4-(3-chloro-phenylamino)-1H-pyrazolo[3,4-d]pyrimidine,
4-(3-chloro-phenylamino)-3-(4-dimethylamino-phenylamino)-1H-pyrazolo[3,4-d]pyrimidine,
4-(3-chloro-phenylamino)-3-(4-methoxy-benzylamino)-1H-pyrazolo[3,4-d]pyrimidine,
4-(3-chloro-phenylamino)-3-(3-methoxy-benzylamino)-1H-pyrazolo[3,4-d]pyrimidine,
4-benzylamino-3-(3-methyl-phenylamino)-1H-pyrazolo[3,4-d]pyrimidine,
(S)-3-(3-methyl-phenylamino)-4-(1-phenyl-ethylamino)-1H-pyrazolo[3,4-d]pyrimidine,
(R)-3-(3-methyl-phenylamino)-4-(1-phenyl-ethylamino)-1H-pyrazolo[3,4-d]pyrimidine,
4-benzylamino-3-(3-chloro-phenylamino)-1H-pyrazolo[3,4-d]pyrimidine,
4-(3-chloro-phenylamino)-3-(3-methoxy-phenylamino)-1H-pyrazolo[3,4-d]pyrimidine,
3-(3-hydroxy-phenyl)-4-(3-chloro-phenylamino)-1H-pyrazolo[3,4-d]pyrimidine,
4-(3-chloro-phenylamino)-3-(4-hydroxy-phenyl)-1H-pyrazolo[3,4-d]pyrimidine,
(R)-3-(3-chloro-phenylamino)-4-(1-phenyl-ethylamino)-1H-pyrazolo[3,4-d]pyrimidine,
(S)-3-(3-chloro-phenylamino)-4-(1-phenyl-ethylamino)-1H-pyrazolo[3,4-d]pyrimidine,
3-(4-acetylamino-benzylamino)-4-(3-chloro-phenylamino)-1H-pyrazolo[3,4-d]pyrimidine,
3-(4-amino-phenylamino)-4-(3-chloro-phenylamino)-1H-pyrazolo[3,4-d]pyrimidine,
4-(3-chloro-phenylamino)-3-(3-hydroxy-phenylamino)-1H-pyrazolo[3,4-d]pyrimidine,
3-(4-amino-benzylamino)-4-(3-chloro-phenylamino)-1H-pyrazolo[3,4-d]pyrimidine,
4-(3-chloro-phenylamino)-3-(4-ethoxy-phenylamino)-1H-pyrazolo[3,4-d]pyrimidine,
4-(3-chloro-phenylamino)-3-(3,4-dimethoxy-phenylamino)-1H-pyrazolo[3,4-d]pyrimidine,
4-(3-chloro-phenylamino)-3-(3,5-dimethoxy-phenylamino)-1H-pyrazolo[3,4-d]pynimidine,
4-(3-chloro-phenylamino)-3-(3-formylamino-4-methoxy-phenylamino)-1H-pyrazolo[3,4-d]-pyrimidine,
3-(3-acetylamino-4-methoxy-phenylamino)-4-(3-chloro-phenylamino)-1H-pyrazolo[3,4-d]-pyrimidine,
3-(4-acetylamino-3-methoxy-phenylamino)-4-(3-chloro-phenylamino)-1H-pyrazolo[3,4-d]-pyrimidine,
4-(3-chloro-phenylamino)-3-(4-formylamino-phenylamino)-1H-pyrazolo[3,4-d]pyrimidine,
4-(3-chloro-phenylamino)-3-(4-formylamino-benzylamino)-1H-pyrazolo[3,4-d]pyrimidine,
4-(3-chloro-phenylamino)-3-(4-propionylamino-benzylamino)-1H-pyrazolo[3,4-d]pyrimidine,
3-(4-aminomethyl-phenylamino)-4-(3-chloro-phenylamino)-1H-pyrazolo[3,4-d]pyrimidine,
3-(3-aminomethyl-phenylamino)-4-(3-chloro-phenylamino)-1H-pyrazolo[3,4-d]pyrimidine,
3-[4-(N-BOC-aminomethyl)-phenylamino]-4-(3-chloro-phenylamino)-1H-pyrazolo[3,4-d]-pyrimidine,
3-[3-(N-BOC-aminomethyl)-phenylamino]-4-(3-chloro-phenylamino)-1H-pyrazolo[3,4-d]-pyrimidine,
3-[4-(N-BOC-amino)-phenylamino]-4-(3-chloro-phenylamino)-1H-pyrazolo[3,4-d]pyrimidine,
4-(3-chloro-phenylamino)-3-(4-methylsulphonylaminomethyl-phenylamino)-1H-pyrazolo[3,4-d]pyrimidine,
4-(3-chloro-phenylamino)-3-(3-methylsulphonylaminomethyl-phenylamino)-1H-pyrazolo[3,4-d]pyrimidine,
4-(3-chloro-phenylamino)-3-(4-formylaminomethyl-phenylamino)-1H-pyrazolo[3,4-d]pyrimidine,
4-(3-chloro-phenylamino)-3-(3-formylaminomethyl-phenylamino)-1H-pyrazolo[3,4-d]pyrimidine,
3-(4-acetylaminomethyl-phenylamino)-4-(3-chloro-phenylamino)-1H-pyrazolo[3,4-d]pyrimidine, and
3-(3-acetylaminomethyl-phenylamino)-4-(3-chloro-phenylamino)-1H-pyrazolo[3,4-d]pyrimidine or a pharmaceutically acceptable salt.

4. A 4-phenylamino-1H-pyrazolo[3,4-d]pyrimidine derivative of formula Ia according to claim 1

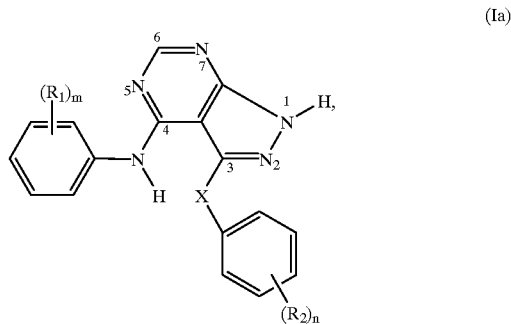

(Ia)

wherein m and n are each independently of the other an integer from 0 up to and including 3, $R_1$ is halogen, cyano, trifluoromethyl, hydroxy, lower alkoxy, lower alkanoyloxy, carboxy, lower alkoxycarbonyl, carbamoyl, N-lower alkylcarbamoyl, or lower alkyl that is unsubstituted or substituted by amino or by cyano, it being possible when several phenyl substituents $R_1$ are present for those substituents to be identical or different from one another, X is the group $NH(CH_2)_t$ wherein t is an integer from 0 up to and including 3, or the group $(C[R_3]-R_4)_q$ wherein q is an integer from 0 up to and including 3 with the proviso that q and n are not simultaneously 0, $R_3$ is hydrogen or lower alkyl and $R_4$ is hydrogen or lower alkyl, and $R_2$ is halogen, nitro, cyano, trifluoromethyl, carboxy, lower alkoxycarbonyl, carbamoyl, N-lower alkylcarbamoyl, amino, lower alkylamino, hydroxy, lower alkanoyloxy, oxa-lower alkoxy, lower alkoxy that is unsubstituted or substituted by carboxy, lower alkoxycarbonyl, carbamoyl or by N-lower alkylcarbamoyl, or lower alkyl that is unsubstituted or substituted by amino or by hydroxy, it being possible when several phenyl substituents $R_2$ are present for those substituents to be identical or different from one another, or a salt of such a compound.

5. A compound of formula Ia according to claim 4, wherein X is the group NH(CH$_2$)$_t$ wherein t is an integer from 0 up to and including 3, or the group (C[R$_3$]—R$_4$)$_q$ wherein q is 0, or a salt of such a compound.

6. A compound of formula Ia according to claim 4, wherein X is the group NH(CH$_2$)$_t$ wherein t is 0, or a salt of such a compound.

7. A compound of formula Ia according to claim 4, wherein m and n are each independently of the other 0 or 1, R$_1$ is halogen, or lower alkyl that is unsubstituted or substituted by amino or by cyano, X is the group NH(CH$_2$)$_t$ wherein t is 0, and R$_2$ is halogen or lower alkoxy, or a salt of such a compound.

8. A compound of formula Ia according to claim 4, selected from 3,4-diphenylamino-1H-pyrazolo[3,4-d]pyrimidine, 3-(3-chloro-phenylamino)-4-phenylamino-1H-pyrazolo[3,4-d]pyrimidine, 3,4-di(3-chloro-phenylamino)-1H-pyrazolo[3,4-d]pyrimidine, 4-(3-bromo-phenylamino)-3-(3-chloro-phenylamino)-1H-pyrazolo[3,4-d]pyrimidine, 3-(3-chloro-phenylamino)-4-(3-methyl-phenylamino)-1H-pyrazolo[3,4-d]pyrimidine, 4-(3-[2-cyano-ethyl]-phenylamino)-3-phenylamino-1H-pyrazolo[3,4-d]pyrimidine, 4-(4-[2-cyano-ethyl]-phenylamino)-3-phenylamino-1H-pyrazolo[3,4-d]pyrimidine, 4-(3-cyanomethyl-phenylamino)-3-phenylamino-1H-pyrazolo[3,4-d]pyrimidine, 3-(3-chloro-phenylamino)-4-(3-methyl-phenylamino)-1H-pyrazolo[3,4-d]pyrimidine, 4-(3-[3-amino-propyl]-phenylamino)-3-phenylamino-1H-pyrazolo[3,4-d]pyrimidine, 4-(4-[3-amino-propyl]-phenylamino)-3-phenylamino-1H-pyrazolo[3,4-d]pyrimidine, 4-(3-[2-amino-ethyl]-phenylamino)-3-phenylamino-1H-pyrazolo[3,4-d]pyrimidine, 3-(4-chloro-phenylamino)-4-(3-chloro-phenylamino)-1H-pyrazolo[3,4-d]pyrimidine, 3-(3-fluoro-phenylamino)-4-(3-chloro-phenylamino)-1H-pyrazolo[3,4-d]pyrimidine, 3-(4-fluoro-phenylamino)-4-(3-chloro-phenylamino)-1H-pyrazolo[3,4-d]pyrimidine, 3-(4-methoxy-phenylamino)-4-(3-chloro-phenylamino)-1H-pyrazolo[3,4-d]pyrimidine, 3-(4-hydroxy-phenylamino)-4-(3-chloro-phenylamino)-1H-pyrazolo[3,4-d]pyrimidine or a pharmaceutically acceptable salt.

9. A pharmaceutical composition comprising a pharmaceutically acceptable carrier or diluent and a therapeutically effective amount of a compound of claim 1, or a pharmaceutically acceptable salt thereof.

10. A method of inhibiting protein tyrosine kinases in a warm-blooded animal comprising administering to said warm-blooded animal a therapeutically effective amount of a 4-amino-1H-pyrazolo[3,4-d]pyrimidine derivative of formula I

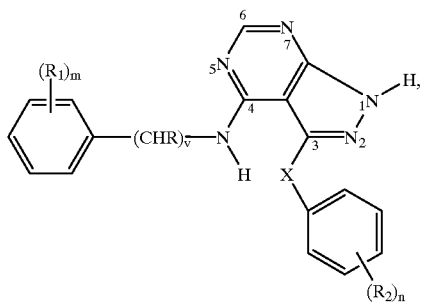

wherein m and n are each independently of the other an integer from 0 up to and including 3, v is 0 or 1, R is hydrogen or lower alkyl, R$_1$ is halogen, cyano, trifluoromethyl, hydroxy, lower alkoxy, lower alkanoyloxy, carboxy, lower alkoxycarbonyl, carbamoyl, N-lower alkylcarbamoyl, or lower alkyl that is unsubstituted or substituted by amino or by cyano, it being possible when several phenyl substituents R$_1$ are present for those substituents to be identical or different from one another, X is the group NH(CH—R$_7$)$_t$ wherein t is an integer from 0 up to and including 3 and R$_7$ is hydrogen or lower alkyl, or the group (C[R$_3$]—R$_4$)$_q$ wherein q is an integer from 0 up to and including 3, R$_3$ is hydrogen or lower alkyl and R$_4$ is hydrogen or lower alkyl, and R$_2$ is halogen, nitro, cyano, trifluoromethyl, carboxy, lower alkoxycarbonyl, carbamoyl, N-lower alkylcarbamoyl, N,N-di-lower alkylcarbamoyl, azido, amino, lower alkylamino, di-lower alkylamino, di-lower alkylamino-lower alkyleneamino, benzylamino, benzoylamino, lower alkanoylamino, lower alkoxycarbonylamino, benzyloxycarbonylamino, thien-2-ylcarbonylamino, fur-2-ylcarbonylamino, pyrid-2-ylcarbonylamino, lower alkylsulfonylamino, benzenesulfonylamino, p-toluenesulfonylamino, hydroxy, lower alkanoyloxy, oxa-lower alkoxy, lower alkoxy that is unsubstituted or substituted by carboxy, lower alkoxycarbonyl, carbamoyl or by N-lower alkylcarbamoyl, or lower alkyl that is unsubstituted or substituted by amino, lower alkanoylamino, benzoylamino, lower alkoxycarbonylamino, lower alkylsulfonylamino, benzenesulfonylamino, p-toluenesulfonylamino, cyano, hydroxy, lower alkanoyloxy, lower alkoxycarbonyloxy or by lower alkoxy, it being possible when several phenyl substituents R$_2$ are present for those substituents to be identical or different from one another and for two vicinal radicals R$_2$ together also to form methylenedioxy, or a pharmaceutically acceptable salt thereof.

11. A method of treating tumors mediated by protein tyrosine kinase inhibition in a warm-blooded animal comprising administering to said warm-blooded animal a therapeutically effective amount of a 4-amino-1H-pyrazolo[3,4-d]pyrimidine derivative of formula I

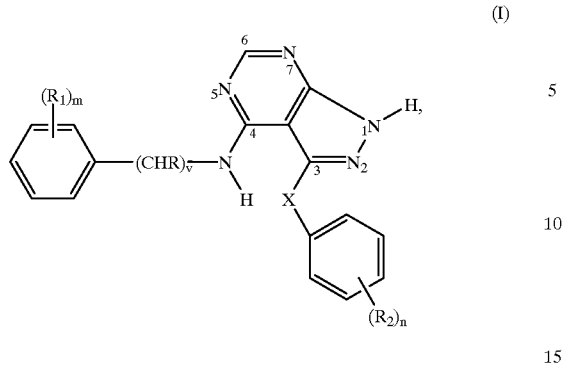 (I)

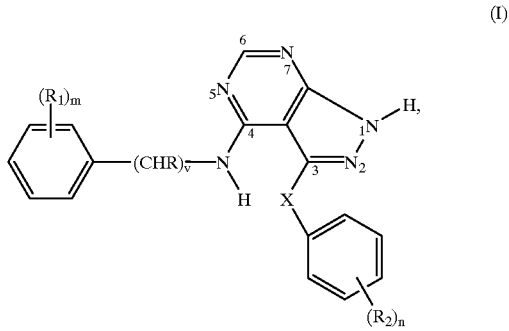 (I)

wherein m and n are each independently of the other an integer from 0 up to and including 3, v is 0 or 1, R is hydrogen or lower alkyl, $R_1$ is halogen, cyano, trifluoromethyl, hydroxy, lower alkoxy, lower alkanoyloxy, carboxy, lower alkoxycarbonyl, carbamoyl, N-lower alkylcarbamoyl, or lower alkyl that is unsubstituted or substituted by amino or by cyano, it being possible when several phenyl substituents $R_1$ are present for those substituents to be identical or different from one another, X is the group $NH(CH-R_7)_t$ wherein t is an integer from 0 up to and including 3 and $R_7$ is hydrogen or lower alkyl, or the group $(C[R_3]-R_4)_q$ wherein q is an integer from 0 up to and including 3, $R_3$ is hydrogen or lower alkyl and $R_4$ is hydrogen or lower alkyl, and $R_2$ is halogen, nitro, cyano, trifluoromethyl, carboxy, lower alkoxycarbonyl, carbamoyl, N-lower alkylcarbamoyl, N,N-di-lower alkylcarbamoyl, azido, amino, lower alkylamino, di-lower alkylamino, di-lower alkylamino-lower alkyleneamino, benzylamino, benzoylamino, lower alkanoylamino, lower alkoxycarbonylamino, benzyloxycarbonylamino, thien-2-ylcarbonylamino, fur-2-ylcarbonylamino, pyrid-2-ylcarbonylamino, lower alkylsulfonylamino, benzenesulfonylamino, p-toluenesulfonylamino, hydroxy, lower alkanoyloxy, oxa-lower alkoxy, lower alkoxy that is unsubstituted or substituted by carboxy, lower alkoxycarbonyl, carbamoyl or by N-lower alkylcarbamoyl, or lower alkyl that is unsubstituted or substituted by amino, lower alkanoylamino, benzoylamino, lower alkoxycarbonylamino, lower alkylsulfonylamino, benzenesulfonylamino, p-toluenesulfonylamino, cyano, hydroxy, lower alkanoyloxy, lower alkoxycarbonyloxy or by lower alkoxy, it being possible when several phenyl substituents $R_2$ are present for those substituents to be identical or different from one another and for two vicinal radicals $R_2$ together also to form methylenedioxy, or a pharmaceutically acceptable salt thereof.

12. A process for preparing a 4-amino-1H-pyrazolo[3,4-d]pyrimidine derivative of formula I wherein m and n are each independently of the other an integer from 0 up to and including 3, v is 0 or 1, R is hydrogen or lower alkyl, $R_1$ is halogen, cyano, trifluoromethyl, hydroxy, lower alkoxy, lower alkanoyloxy, carboxy, lower alkoxycarbonyl, carbamoyl, N-lower alkylcarbamoyl, or lower alkyl that is unsubstituted or substituted by amino or by cyano, it being possible when several phenyl substituents $R_1$ are present for those substituents to be identical or different from one another, X is the group $NH(CH-R_7)_t$ wherein t is an integer from 0 up to and including 3 and $R_7$ is hydrogen or lower alkyl, or the group $(C[R_3]-R_4)_q$ wherein q is an integer from 0 up to and including 3, $R_3$ is hydrogen or lower alkyl and $R_4$ is hydrogen or lower alkyl, and $R_2$ is halogen, nitro, cyano, trifluoromethyl, carboxy, lower alkoxycarbonyl, carbamoyl, N-lower alkylcarbamoyl, N,N-di-lower alkylcarbamoyl, azido, amino, lower alkylamino, di-lower alkylamino, di-lower alkylamino-lower alkyleneamino, benzylamino, benzoylamino, lower alkanoylamino, lower alkoxycarbonylamino, benzyloxycarbonylamino, thien-2-ylcarbonylamino, fur-2-ylcarbonylamino, pyrid-2-ylcarbonylamino, lower alkylsulfonylamino, benzenesulfonylamino, p-toluenesulfonylamino, hydroxy, lower alkanoyloxy, oxa-lower alkoxy, lower alkoxy that is unsubstituted or substituted by carboxy, lower alkoxycarbonyl, carbamoyl or by N-lower alkylcarbamoyl, or lower alkyl that is unsubstituted or substituted by amino, lower alkanoylamino, benzoylamino, lower alkoxycarbonylamino, lower alkylsulfonylamino, benzenesulfonylamino, p-toluenesulfonylamino, cyano, hydroxy, lower alkanoyloxy, lower alkoxycarbonyloxy or by lower alkoxy, it being possible when several phenyl substituents $R_2$ are present for those substituents to be identical or different from one another and for two vicinal radicals $R_2$ together also to form methylenedioxy, or a salt of such a compound, which process comprises treating a compound of formula II

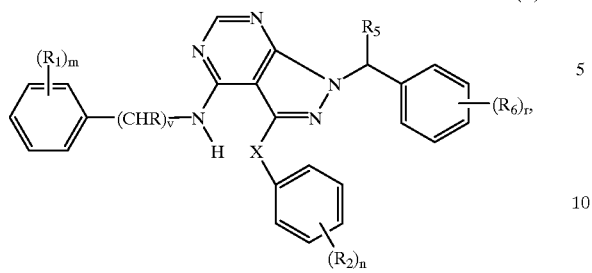
(II)
wherein $R_5$ is hydrogen or methyl, $R_6$ is alkoxy having from 1 to 3 carbon atoms or is nitro, r is an integer from 0 to 2, and the remaining substituents and symbols are as defined above, with a suitable Lewis acid, and, if desired, converting a compound of formula I into its salt, or converting an obtainable salt of a compound of formula I into the free compound.
* * * * *

UNITED STATES PATENT AND TRADEMARK OFFICE
CERTIFICATE OF CORRECTION

PATENT NO  : 5,981,533
DATED:     : November 9, 1999
INVENTOR(S) : TRAXLER ET AL.

It is certified that there is an error in the above-identified patent and that said Letters Patent is hereby corrected as shown below:

Claim 3, in column 52, line 32 should read:

-- 4-(3-chloro-phenylamino)-3-(4-[{N,N-dimethylamino}- --.

Claim 3, in column 52, line 35 should read:

-- 4-(3-chloro-phenylamino)-3-(3-[{N,N-dimethylamino}- --.

Claim 3, in column 53, line 50 should read:

-- phenylamino)-1H-pyrazolo[3,4-d]pyrimidine, --.

Signed and Sealed this

Sixth Day of March, 2001

Attest:

NICHOLAS P. GODICI

Attesting Officer    Acting Director of the United States Patent and Trademark Office